US007189697B2

(12) United States Patent
Panjwani

(10) Patent No.: US 7,189,697 B2
(45) Date of Patent: Mar. 13, 2007

(54) COMPOSITIONS AND USES OF A GALECTIN FOR TREATMENT OF DRY EYE SYNDROME

(75) Inventor: Noorjahan Panjwani, Medford, MA (US)

(73) Assignee: Trustees of Tufts College, Boston, MA (US)

( * ) Notice: Subject to any disclaimer, the term of this patent is extended or adjusted under 35 U.S.C. 154(b) by 52 days.

(21) Appl. No.: 11/104,677

(22) Filed: Apr. 13, 2005

(65) Prior Publication Data
US 2006/0189514 A1 Aug. 24, 2006

Related U.S. Application Data

(60) Provisional application No. 60/634,361, filed on Dec. 8, 2004, provisional application No. 60/562,030, filed on Apr. 13, 2004.

(51) Int. Cl.
*A61K 38/17* (2006.01)
(52) U.S. Cl. .......................................... 514/12; 530/350
(58) Field of Classification Search ...................... None
See application file for complete search history.

(56) References Cited

U.S. PATENT DOCUMENTS 6,967,021 B2 * 11/2005 Panjwani et al. ......... 424/185.1
2002/0044932 A1 * 4/2002 Liu et al. ................. 424/143.1

OTHER PUBLICATIONS

Sall et al., Two Multicenter, Randomized Studies of the Efficacy and Safety of Cylosporine Ophthalmic Emulsion in Moderate to Severe Dry Eye Disease, Ophthalmology, 2000, vol. 107, pp. 631-639.*
Solomon et al., Pro- and Anti-inflammatory Forms of Interleukin-1 in the Tear Fluid and Conjunctiva of Patients with Dry-Eye Disease, Investigative Ophthalmology & Visual Science, 2001, vol. 42, pp. 2283-2292.*
Accession No. AAB02856 in GenBank.
Accession No. BAA22164 in GenBank, Seq Id No. 1.
Accession No. CAA55479 in GenBank.
Accession No. I55469 in GenBank, Seq Id No. 2.
Accession No. JC4300 in GenBank.
Accession No. O54974 in GenBank.
Accession No. P97590 in GenBank.
Accession No. O00214 in GenBank.
Accession No. Q8TEV1 in GenBank.
Abelson et al., 2003, Rev Ophthalmol 10:1.
Bernerd et al., 1999, Proc. Natl. Acad. Sci. USA 96:11329-11334.
Bresalier et al., 1996, Cancer Res 56:4354-4357.
Brewitt et al. 2001, Surv of Ophthalmol 45:S199-S202.
Burgalassi et al., 1999, Ophthalm Res 31:229-235.
Cao et al., 2002, J Biol Chem 277:42299-42305.
CAO et al., 2003, Arch Ophthalmol 121:82-86.
Cherayil et al., 1990, Proc. Natl. Acad. Sci. USA 87:7324-7328.
Dagher et al., 1995, Proc. Natl. Acad. Sci. USA 92:1213-1217.
Danjo et al., 1998, Invest Ophthalmol Vis Sci 39:2602-2609.
Dursun et al., 2002, Invest Ophthamol & Vis Sci 43:632-638.
Foulks, 2003, The Ocular Surface, 1:20-30.
Gamache et al., 2000, Cornea 19:6:S88.
Gilbard, 2000, "Dry-eye Disorders," In: Albert M et al., ed. Principles and Practice of Ophthalmology: 2nd Edition, Philadelphia: W.B. Saunders Company: 982-1001.
Gipson et al., 1997, Prog Retinal Eye Res 16:1:81-98.
Hadari et al., 1997, Trends in Glycosci and Glycotechnol 9:103-112.
Hsu et al., 2000, Am J Pathol 156:1073-1083.
Jabs et al., 1991, Invest Opthamol Vis Sci 32:371-380.
Jabs et al., 1997, Curr Eye Res 16:909-916.
Jeng et al., 1994, Immunol Lett 42:113-116.
Jumblatt et al., 1998, Exp Eye Res 67:341-346.
Leonidas et al., 1998, Biochemistry 37:13930-13940.
Liu, 2000, Clin Immunology 97:79-88.
Liu et al., 1996, Biochemistry 35:6073-6079.
Madsen et al., 1995, J Biol Chem 270:5823-5829.
Magnaldo et al., 1995, Develop Biol 168:259-271.
Matarrese et al., 2000, Int J Cancer 85:545-554.
Perillo et al., 1998, J Mol Med 76:402-412.
Pflugfelder, 2003, The Ocular Surface, 1:31-36.
Rolando et al., 2001, Surv Ophthalmol 45:S203-S210.
Schein et al., 1997, Am J Ophthalmol 124:723-728.
Seelenmeyer et al., 2003, J Cell Sci, 116:1305-1318.
Seetharaman et al., 1998, J Biol Chem 273:13047-13052.
Singh et al., 1989, Cornea 8:45-53.
Timmons et al., 1999, Int J Dev Biol 43:229-235.
Wang et al., 1995, Biochem Biophys Res Commun 217:292-303.
Warfield et al., 1997, Invasion Metastasis 17:101-112.
Watanabe, 2002, Cornea 21:S17-S22.
Yang et al., 1998, Biochemistry 37:4086-4092.
Zoukhri et al., 2001, Invest Ophthalmol Vis Sci 42:925-932.

* cited by examiner

*Primary Examiner*—Robert A. Wax
(74) *Attorney, Agent, or Firm*—Lawson & Weitzen, LLP; Sonia K. Guterman; Adam M. Schoen

(57) ABSTRACT

Methods for the therapeutic treatment of dry eye in mammals comprising administering to a mammal afflicted with an epithelial wound a therapeutically effective amount of a galectin-1 protein, a galectin-3, a galectin-7 protein and/or a galectin-8 protein are provided. Pharmaceutical and ophthalmic compositions and kits, comprising a pharmaceutically active agent which is a galectin-1 protein, a galectin-3 protein, galectin-7 protein and/or a galectin-8 protein, and a suitable carrier or a diluent, are provided.

26 Claims, 21 Drawing Sheets

Human galectin-3 (SEQ ID NO.1):

```
  1 MADNFSLHDA LSGSGNPNPQ GWPGAWGNQP AGAGGYPGAS YPGAYPGQAP PGAYPGQAPP
 61 GAYHGAPGAY PGAPAPGVYP GPPSGPGAYP SSGQPSAPGA YPATGPYGAP AGPLIVPYNL
121 PLPGGVVPRM LITILGTVKP NANRIALDFQ RGNDVAFHFN PRFNENNRRV IVCNTKLDNN
181 WGREERQSVF PFESGKPFKI QVLVEPDHFK VAVNDAHLLQ YNHRVKKLNE ISKLGISGDI
241 DLTSASYTMI
```

Amino acid composition (250 amino acids, molecular wt: 26174.2 Da)

| aa |  # | mole% |  wt%  |
|----|----|-------|-------|
| A Ala | 27 | 10.80 | 7.33 |
| C Cys |  1 |  0.40 | 0.39 |
| D Asp |  9 |  3.60 | 3.96 |
| E Glu |  6 |  2.40 | 2.96 |
| F Phe |  9 |  3.60 | 5.06 |
| G Gly | 34 | 13.60 | 7.41 |
| H His |  6 |  2.40 | 3.14 |
| I Ile | 10 |  4.00 | 4.32 |
| K Lys |  8 |  3.20 | 3.92 |
| L Leu | 15 |  6.00 | 6.49 |
| M Met |  3 |  1.20 | 1.51 |
| N Asn | 18 |  7.20 | 7.85 |
| P Pro | 36 | 14.40 | 13.36 |
| Q Gln |  9 |  3.60 | 4.41 |
| R Arg |  9 |  3.60 | 5.37 |
| S Ser | 14 |  5.60 | 4.66 |
| T Thr |  6 |  2.40 | 2.32 |
| V Val | 14 |  5.60 | 5.30 |
| W Trp |  3 |  1.20 | 2.13 |
| Y Tyr | 13 |  5.20 | 8.11 |

FIGURE 1

Human galectin-7 (SEQ ID NO.2):

```
  1 MSNVPHKSSL PEGIRPGTVL RIRGLVPPNA SRFHVNLLCG EEQGSDAALH FNPRLDTSEV
 61 VFNSKEQGSW GREERGPGVP FQRGQPFEVL IIASDDGFKA VVGDAQYHHF RHRLPLARVR
121 LVEVGGDVQL DSVRIF
```

Amino acid composition (136 amino acids, molecular wt: 15059.1 Da)

| aa |     | #  | mole% | wt%   |
|----|-----|----|-------|-------|
| A  | Ala | 7  | 5.15  | 3.30  |
| C  | Cys | 1  | 0.74  | 0.68  |
| D  | Asp | 7  | 5.15  | 5.35  |
| E  | Glu | 9  | 6.62  | 7.72  |
| F  | Phe | 8  | 5.88  | 7.82  |
| G  | Gly | 14 | 10.29 | 5.31  |
| H  | His | 6  | 4.41  | 5.46  |
| I  | Ile | 5  | 3.68  | 3.76  |
| K  | Lys | 3  | 2.21  | 2.55  |
| L  | Leu | 12 | 8.82  | 9.02  |
| M  | Met | 1  | 0.74  | 0.87  |
| N  | Asn | 5  | 3.68  | 3.79  |
| P  | Pro | 10 | 7.35  | 6.45  |
| Q  | Gln | 6  | 4.41  | 5.11  |
| R  | Arg | 13 | 9.56  | 13.48 |
| S  | Ser | 10 | 7.35  | 5.78  |
| T  | Thr | 2  | 1.47  | 1.34  |
| V  | Val | 15 | 11.03 | 9.88  |
| W  | Trp | 1  | 0.74  | 1.24  |
| Y  | Tyr | 1  | 0.74  | 1.08  |

FIGURE 2

```
CLUSTAL W (1.81) Multiple Sequence Alignments

Sequence 1: gi|2385452|dbj|BAA22164.1|      250 aa
Sequence 2: gi|1363962|pir||JC4300          242 aa
Sequence 3: gi|1389600|gb|AAB02856.1|       262 aa
Sequence 4: gi|535083|emb|CAA55479.1|       245 aa Sequences (2:3) Aligned. Score: 58    Sequences (3:4) Aligned. Score: 52
Sequences (1:3) Aligned. Score: 55    Sequences (1:2) Aligned. Score: 82
Sequences (1:4) Aligned. Score: 84    Sequences (2:4) Aligned. Score: 78

Group 1: Sequences:    2    Score:4935
Group 2: Sequences:    3    Score:4768
Group 3: Sequences:    4    Score:3929
Alignment Score 6348
```

```
Human galectin-3     ----------------MADNFSLHDALSGSGNPNPQGWPGAWG-NQPAG  32
Hamster galectin-3   ----------------MADGFSLNDALAGSGNPNPQGWPGAWG-NQP-G  31
Rabbit galectin-3    ----------------MADGFSLNDALSGSGHPPNQGWPGPWG-NQPAG  32
Chicken galectin-3   MQAMKARCWQPHWMLPLLPLSSPLHPQLSDALPAHNPGAPPPQGWNRPPG  50
                                     :  .  *:  *:. .    * * . * * *:*  *

Human galectin-3     AGGYPG-ASYPGAYPGQAPPGAYPGQAPPGAYPG--APGAYPGAPAPGVY  79
Hamster galectin-3   AGGYPG-ASYPGAYPGQAPPGAYPGQAPPGAYPGPTAPGAYPG-PAPGAY  79
Rabbit galectin-3    PGGYPG-AAYPGAYPGHAP-GAYPGQAPPGPYPG-------PG--AHGAY  71
Chicken galectin-3   PGAFPAYPGYPGAYP--GAPGPYPG--APGPHHG--PPGPYPG-GPPGPY  93
                     .*.:*. ..****       *.*** .**.:  *        **  .  * *

Human galectin-3     PGPPSGPGAYPSSGQPSATGAYPA--TGPYG-APAGPLIVPYNLPLPGGV  126
Hamster galectin-3   PGQPGASGAYP-----SAPGAYPA--AGPYG-APTGALTVPYKLPLAGGV  121
Rabbit galectin-3    PGQPGGPGAYPSPGQPSGAGAYPG--ASPYS-ASAGPLPVPYDLPLPGGV  118
Chicken galectin-3   PGGP--PGPYPG----GPPGPYPGGPTAPYSEAPAAPLKVPYDLPLPAGL  137
                     ** *   .*.**    . *.**.   :.**. *.:..* ***.***..*:

Human galectin-3     VPRMLITILGTVKPNANRIALDFQRGNDVAFHFNPRFNENNRRVIVCNTK  176
Hamster galectin-3   MPRMLITIMGTVKPNANRIILNFLRGNDIAFHFNPRFNENNRRVIVCNTK  171
Rabbit galectin-3    MPRMLITIVGTVKPNANRLALDFKRGNDVAFHFNPRFNENNRRVIVCNTK  168
Chicken galectin-3   MPRLLITITGTVNSNPNRFSLDFKRGQDIAFHFNPRFKEDHKRVIVCNSM  187
                     :**:****  ***:.*:**: *.*:.*:*.**********:*:::*****:

Human galectin-3     LDNNWGREERQS-VFPFESGKPFKIQVLVEPDHFKVAVNDAHLLQYNHRV  225
Hamster galectin-3   QDNNWGREERQS-AFPFESGRPFKIQVLVEADHFKVAVNDAHLLQYNHRM  220
Rabbit galectin-3    VDNNWGREERQT-TFPFEIGKPFKIQVLVEPDHFKVAVNDAHLLQYNHRM  217
Chicken galectin-3   FQNNWGKEERTAPRFPFEPGTPFKLQVLCEGDHFKVAVNDAHLLQFNFRE  237
                      :****:*** :   ****  * ***:*** * ************:* *

Human galectin-3     KKLNEISKLGISGDIDLTSASYTMI  250
Hamster galectin-3   KNLREINQMEISGDITLTSAAPTMI  245
Rabbit galectin-3    RNLKEINKLGISGDIQLTSASHAMI  242
Chicken galectin-3   KKLNGITKLCIAGDITLTSVLTSMI  262
                     ::*. *.:: ***** ***.   :**
```

FIGURE 3

```
CLUSTAL W (1.81) Multiple Sequence Alignments

Sequence 1: gi|2135152|pir||I55469              136 aa
Sequence 2: gi|3915736|sp|P97590|LEG7_RAT        136 aa
Sequence 3: gi|3913978|sp|O54974|LEG7_MOUS       136 aa Sequences (2:3) Aligned. Score:  88
Sequences (1:2) Aligned. Score:  72
Sequences (1:3) Aligned. Score:  78

Group 1: Sequences:   2        Score:2837
Group 2: Sequences:   3        Score:2646
Alignment Score 2151

Rat galectin-7      MSATHHKTPLPQGVRLGTVMRIRGVVPDQAGRFHVNLLCGEEQEADAALH 50
Mouse galectin-7    MSATHHKTSLPQGVRVGTVMRIRGLVPDQAGRFHVNLLCGEEQGADAALH 50
Human galectin-7    MSNVPHKSSLPEGIRPGTVLRIRGLVPPNASRFHVNLLCGEEQGSDAALH 50
                    **  .**:.**:*:* ***:****:** ..:************ :****

Rat galectin-7      FNPRLDTSEVVFNTKQQGKWGREERGTGIPFQRGQPFEVLIITTEEGFKT 100
Mouse galectin-7    FNPRLDTSEVVFNTKQQGKWGREERGTGIPFQRGQPFEVLLIATEEGFKA 100
Human galectin-7    FNPRLDTSEVVFNSKEQGSWGREERGPGVPFQRGQPFEVLIIASDDGFKA 100
                    *************.*:**.******* *:***********:**::.***:

Rat galectin-7      VIGDDEYLHFHHRMPSSNVRSVEVGGDVQLHSVKIF 136
Mouse galectin-7    VVGDDEYLHFHHRLPPARVRLVEVGGDVQLHSLNIF 136
Human galectin-7    VVGDAQYHHFRHRLPLARVRLVEVGGDVQLDSVRIF 136
                    *:** :* **:**:*  .** *********.*:.**
```

FIGURE 4

PROSITE SCAN of Human galectin-3 (SEQ ID NO.1)

N-glycosylation site (PROSITE: PS00001)

4-7 NFSL

Protein kinase C phosphorylation site (PROSITE: PS00005)

137-139 TVK
194-196 SGK

Casein kinase II phosphorylation site (PROSITE: PS00006)

6-9 SLHD
175-178 TKLD

N-myristoylation site (PROSITE: PS00008)

24-29 GAWGNQ
27-32 GNQPAG
34-39 GGYPGA
43-48 GAYPGQ
52-57 GAYPGQ
61-66 GAYPGA
65-70 GAPGAY
68-73 GAYPGA

Galaptin signature sequence (PROSITE: PS00309)

181-200 WGREERQSVFPFESGKPFKI

FIGURE 5

PROSITE SCAN of Human galectin-7 (SEQ ID NO.2)

N-glycosylation site (PROSITE: PS00001)

29-32 NASR

Protein kinase C phosphorylation site (PROSITE: PS00005)

132-134 SVR

Casein kinase II phosphorylation site (PROSITE: PS00006)

9-12 SLPE

N-myristoylation site (PROSITE: PS00008)

13-18 GIRPGT
44-49 GSDAAL

Galaptin signature sequence (PROSITE: PS00309)

70-89 WGREERGPGVPFQRGQPFEV

FIGURE 6

PFAM 7.0 HMM Sequence Alignment

PF00337 (Galactoside-binding lectin domain) score 217.2, E = 1.3e-62

```
PF00337                *->pglvalnlglkpGktltVkGtVapknakrFavNlgkgskEEndlvLH
                          p+  +l++g+ p++ +t+ GtV p na+r a+++ +g    nd+++H
Human galectin-3   117  PYNLPLPGGVVPRMLITILGTVKP-NANRIALDFQRG----NDVAFH  158

PF00337                 fNPRFneaHGDqntvVcNSkenGDNeWGtEqReaafPFqaGqpFeisIsv
                        fNPRFne +   +++VcN+k+++  +WG E+R+   fPF++G+pF+i++ v
Human galectin-3   159  FNPRFNENN--RRVIVCNTKLDN--NWGREERQSVFPFESGKPFKIQVLV  204

PF00337                 eedkfkVkvndghefeFphRlk.leavqyLgikGDikltsikf<-*
                        e+d+fkV+vnd+h+++++hR k+l ++++Lgi+GDi+lts+++
Human galectin-3   205  EPDHFKVAVNDAHLLQYNHRVKkLNEISKLGISGDIDLTSASY     247
```

FIGURE 7

PFAM 7.0 HMM Sequence Alignment

PF00337 (Galactoside-binding lectin domain) score 124.0, E = 1.6e-34

```
PF00337            *->pglvalnlglkpGktltVkGtVapknakrFavNlgkgskEEndlvLH
                      p  + l++g +pG  l+++G+V p na rF+vNl+ g    +d +LH
Human galectin-7  5   PHKSSLPEGIRPGTVLRIRGLVPP-NASRFHVNLLCGEEQGSDAALH  50

PF00337               fNPRFneaHGDqntvVcNSkenGDNeWGtEqReaafPFqaGqpFeisIsv
                      fNPR + +       vV NSke G  +WG E+R +  PFq+GqpFe+ I
Human galectin-7  51  FNPRLDTSE-----VVFNSKEQG--SWGREERGPGVPFQRGQPFEVLIIA  93

PF00337               eedkfkVkvndghefeFphRlkleavqyLgikGDikltsikf<-*
                      d fk  v d+ + +F hRl+l +v  +++ GD+ l+s+ +
Human galectin-7  94  SDDGFKAVVGDAQYHHFRHRLPLARVRLVEVGGDVQLDSVRI     135
```

FIGURE 8

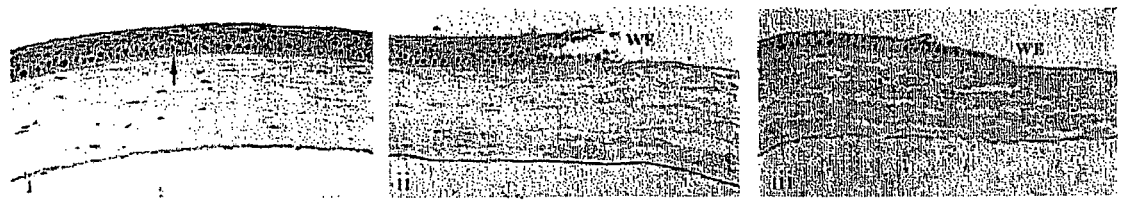
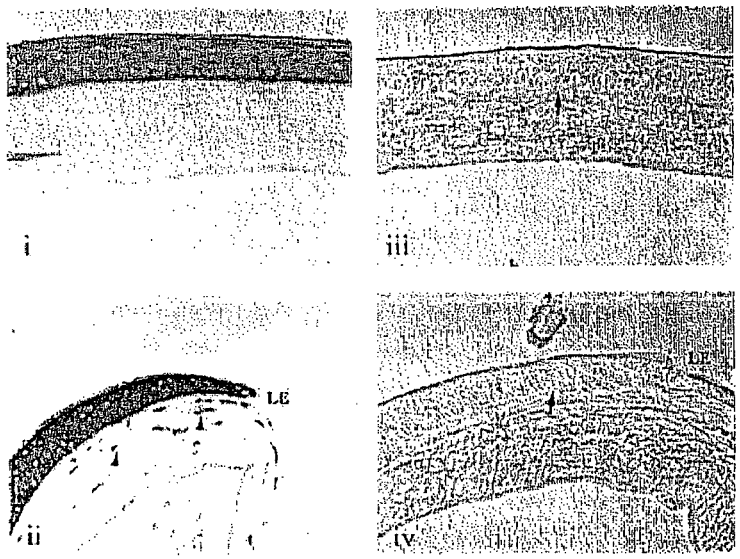
FIGURE 9

A
Microarray data

| Gene | Fold △ |
|---|---|
| Galectin-7 | 11.7↓ |
| GAPDH | 1.0 (NC) |
| RPS29 | 1.1↓ |
| ODC | 1.2↓ |

B
Semi-quantitative RT-PCR

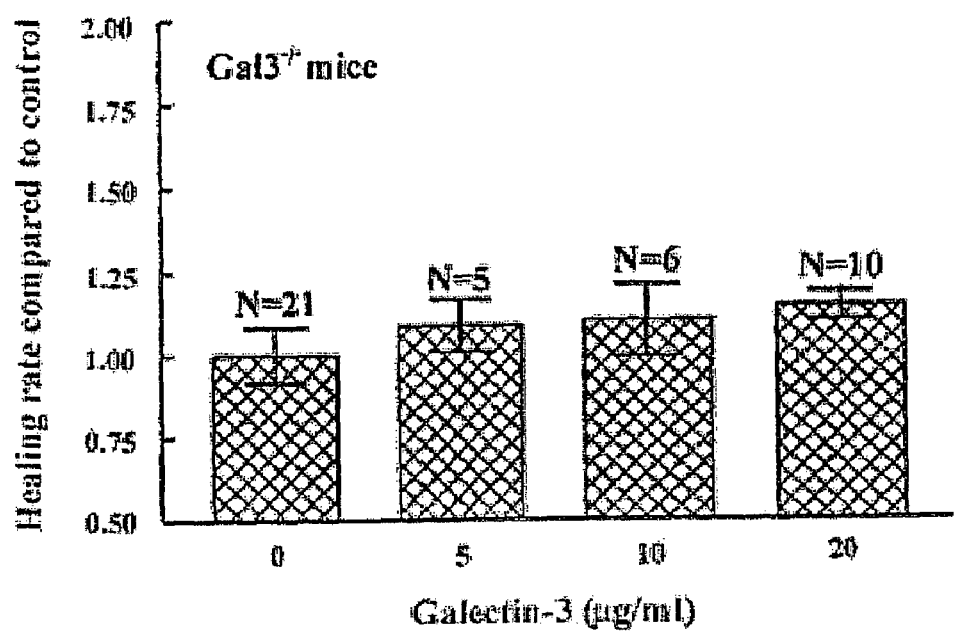
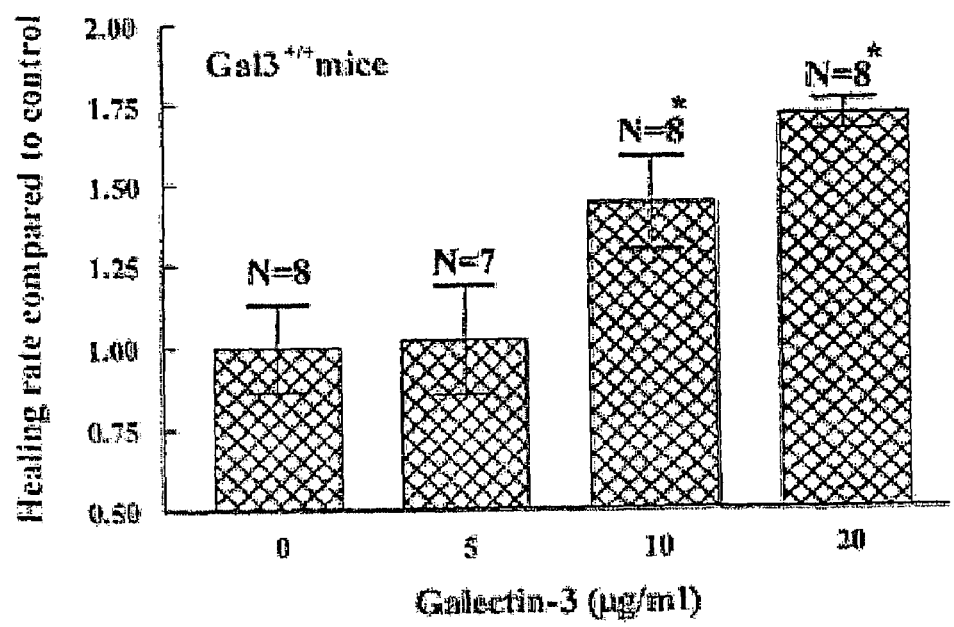
FIGURE 14

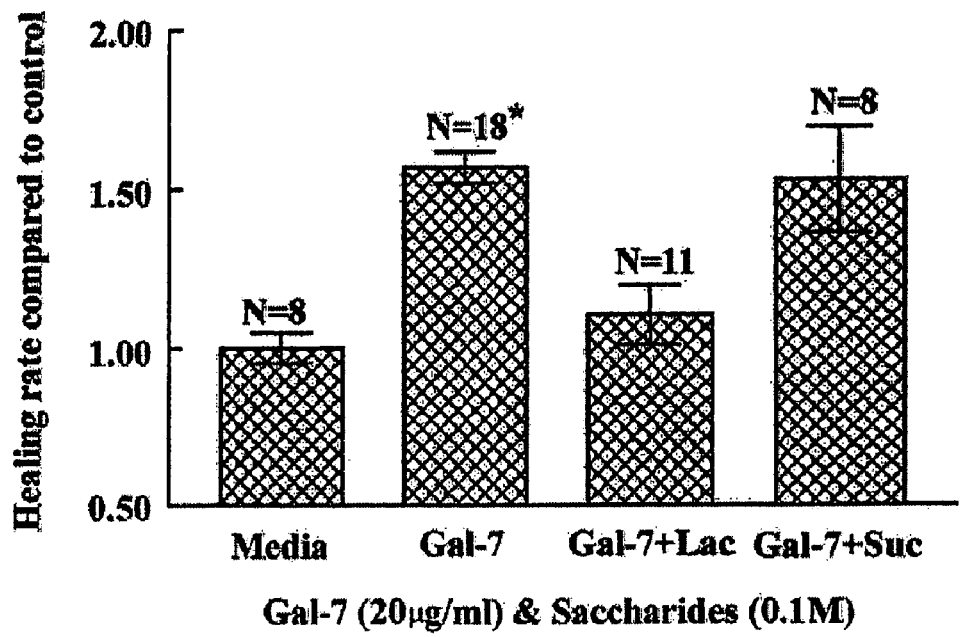
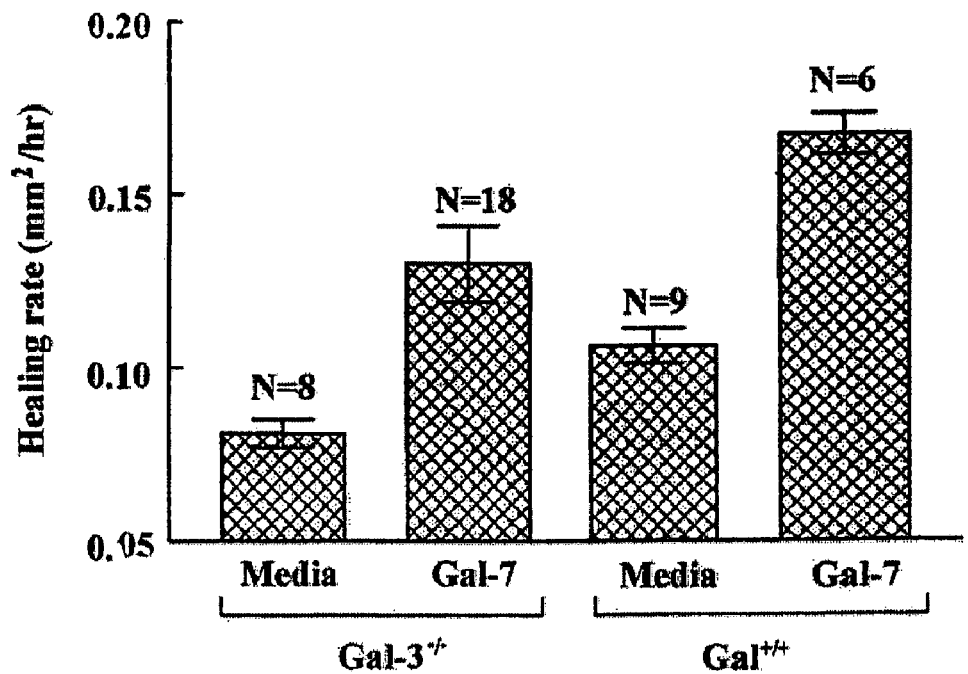
FIGURE 16

Human galectin-1 (SEQ ID NO. 6):

```
1   MACGLVASNL NLKPGECLRV RGEVAPDAKS FVLNLGKDSN NLCLHFNPRF

51  NAHGDANTIV CNSKDGGAWG TEQREAVFPF QPGSVAEVCI TFDQANLTVK

101 LPDGYEFKFP NRLNLEAINY MAADGDFKIK CVAFD
```

FIGURE 17

Human Galectin-8 (SEQ ID NO. 4):

```
1   MMLSLNNLQN IIYNPVIPFV GTIPDQLDPG TLIVIRGHVP SDADRFQVDL
51  QNGSSMKPRA DVAFHFNPRF KRAGCIVCNT LINEKWGREE ITYDTPFKRE
101 KSFEIVIMVL KDKFQVAVNG KHTLLYGHRI GPEKIDTLGI YGKVNIHSIG
151 FSFSSDLQST QASSLELTEI SRENVPKSGT PQLRLPFAAR LNTPMGPGRT
201 VVVKGEVNAN AKSFNVDLLA GKSKDIALHL NPRLNIKAFV RNSFLQESWG
251 EEERNITSFP FSPGMYFEMI IYCDVREFKV AVNGVHSLEY KHRFKELSSI
301 DTLEINGDIH LLEVRSW
```

FIGURE 18

Galectin-1

```
Human galectin-1    MACGLVASNL NLKPGECLRV RGEVAPDAKS FVLNLGKDSN NLCLHFNPRF NAHGDANTIV CNSKDDGAWG
Rat galectin-1      MACGLVASNL NLKPGECLKV RGELAPDAKS FVLNLGKDSN NLCLHFNPRF NAHGDANTIV CNSKDDGTWG
Mouse galectin-1    MACGLVASNL NLKPGECLKV RGEVASDAKS FVLNLGKDSN NLCLHFNPRF NAHGDANTIV CNTKEDGTWG
Hamster galectin-1  MACGLVASNL NLKPGECLKV RGEVAPDAKS FVLNLGKDSN NLCLHFNPRF NAHGDANTIV CNSKDNGAWG Human galectin-1    TEQREAVFPF QPGSVAEVCI TFDQANLTVK LPDGYEFKFP NRLNLEAINY MAADGDFKIK CVAFD
Rat galectin-1      TEQRETAFPF QPGSITEVCI TFDQADLTIK LPDGHEFKFP NRLNMEAINY MAADGDFKIK CVAFE
Mouse galectin-1    TEHREPAFPF QPGSITEVCI TFDQADLTIK LPDGHEFKFP NRLNMEAINY MAADGDFKIK CVAFE
Hamster galectin-1  TEHREPAFPF QPGSIVEVCI TFDQADLTIK LPDGHEFKFP NRLNMEAINY MAADGDFKIK CVAFE
```

FIGURE 19

Galectin-8

```
Human   MMLSLNNLQNIIYNPVIPFVGTIPDQLDPGTLIVIRGHVPSDADRFQVDLQNGSSMKPRADVAFHFNPRFKRAGCIVCNTL
Mouse   MLSLNNLQNIIYNPIIPYVGTIPYVGTITEQLKPGSLIVIRGHVPKDSERFQVDFQLGNSLKPRADVAFHFNPRFKRSSCIVCNTL
Rat     MLSLSNLQNIIYNPTIPYVSTITEQLKPGSLIVIRGHVPKDSERFQVDFQHGNSLKPRADVAFHFNPRFKRSNCIVCNTL
Chicken MMSLDGPQKKISNPIIPYVGTILGGLVPGELIVLHGSVPDDADRFQVDLQCGSSEKPRADVAFHFNPRFKWSGOVVCNTL
Frog    MAQTG_LQRTIMDPVVPVPVGTIFGGLEPGQMIVLHGTVHPDADRFQIDFQRGNSVQPRSDVAFHFNPRFKGSGHIVCNTL Human   INEKWGREEITYDTPFKREKSFEIVIMVLKDKFQVAVNGKHTLLYGHRIGPEKIDTLGIYGKVNIHSIGFSFSSDLQSTQA
Mouse   TQEKWGWEEITYDMPFRKEKSFEIVFMVLRNKFQVAVNGRHVLLYAHRISPEQIDTVGIYGKVNIHSIGFRFSSDLQSMET
Rat     TNEKWGWEEITHDMPFRKEKSFEIVIMVLKNKFHVAVNGKHILLYAHRINPEKIDTLGIEGKVNIHSIGFRFSSDLQSMET
Chicken EREKWGWEEITYEMPFQKGRPFEIVIMLLKDKFQVSVNKKHLLIYNHRISLERIDTLGIYGKVQIKSIEFV_SNSVQGAQP
Frog    ENEKWGWEEKTYQMPFTKGQPFEIIFLVEHDKFQVSSNGKNLLVYKHRISLQRVDTLGISGKVKINTIGFLAQPTLLGSQP Human   SSLELTEISRENVPKSGTPQLRLPFAARLNTPMGPGRTVVVKGEVNANAKSFNVDLLAGKSKDIALHLNPRLNIKAFVRNS
Mouse   SALGLTQINRENIQKPGKLQLSLPFEARLNASMGPGRTVVIKGEVNTNARSFNVDLVAGKTRDIALHLNPRLNVKAFVRNS
Rat     STLGLTQISKENIQKSGKLHLSLPFEARLNASMGPGRTVVWKGEVNTNATSFNVDLVAGRSRDIALHLNPRLNVKAFVRNS
Chicken SSVGVTKINTENGEMPDGLQFGVPYVGKLVSALHPGCTVAIKGEVNKNPKSFINLKSSDSKDIALHLNPRLNKVFVRNS
Frog    TSLAGNSIEANKGGSEKPRNFTIPYTGCLPSPLIPGKTMVIKGEVLKNAKRFAIDLKPHGSKDIALHLNPRMKERVFVRNT Human   FLQESWGEEERNITSFPFSPGMYFEMIIYCDVREFKVAVNGVHSLEYKHRFKELSSIDTLEINGDIHLLEVRSW
Mouse   FLQDAWGEEERNITCFPFSSGMYFEMIIYCDVREFKVAINGVHSLEYKHRFKDLSSIDTLSVDGDTRLLDVRSW
Rat     FLQDAWGEEERNITCFPFSSGMYFEMIIYCDVREFKVAVNGVHSLEYKHRFKDLSSIDTLAVDGDTRLLDVRSW
Chicken YLHDSWGEEEKEVTNFPFSPGMYFELIIFCDAHOFFKVAVNGVHTLEYKHRFKQLEKINLIEVTGDVQLLDVRSW
Frog    YLRESWGEEEKQLLDFPFCPEMYFELLIYCDLQQFRVAVNGVHLLEYKHRFKDLNKINEVSVNGDIQLHDVRIW
```

FIGURE 20

SEQUENCE LISTING

<160> NUMBER OF SEQ ID NOS: 6

<210> SEQ ID NO 1
<211> LENGTH: 250
<212> TYPE: PRT
<213> ORGANISM: Homo sapiens

<400> SEQUENCE: 1

Met Ala Asp Asn Phe Ser Leu His Asp Ala Leu Ser Gly Ser Gly Asn
1               5                   10                  15

```
Pro Asn Pro Gln Gly Trp Pro Gly Ala Trp Gly Asn Gln Pro Ala Gly
            20                  25                  30

Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr His
    50                  55                  60

Gly Ala Pro Gly Ala Tyr Pro Gly Ala Pro Ala Pro Gly Val Tyr Pro
65                  70                  75                  80

Gly Pro Pro Ser Gly Pro Gly Ala Tyr Pro Ser Ser Gly Gln Pro Ser
            85                  90                  95

Ala Pro Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
        115                 120                 125

Arg Met Leu Ile Thr Ile Leu Gly Thr Val Lys Pro Asn Ala Asn Arg
    130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190

Glu Ser Gly Lys Pro Phe Lys Ile Gln Val Leu Val Glu Pro Asp His
        195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
                245                 250

<210> SEQ ID NO 2
<211> LENGTH: 136
<212> TYPE: PRT
<213> ORGANISM: Homo sapiens

<400> SEQUENCE: 2

Met Ser Asn Val Pro His Lys Ser Ser Leu Pro Glu Gly Ile Arg Pro
1               5                   10                  15

Gly Thr Val Leu Arg Ile Arg Gly Leu Val Pro Pro Asn Ala Ser Arg
            20                  25                  30

Phe His Val Asn Leu Leu Cys Gly Glu Glu Gln Gly Ser Asp Ala Ala
        35                  40                  45

Leu His Phe Asn Pro Arg Leu Asp Thr Ser Glu Val Val Phe Asn Ser
    50                  55                  60

Lys Glu Gln Gly Ser Trp Gly Arg Glu Glu Arg Gly Pro Gly Val Pro
65                  70                  75                  80

Phe Gln Arg Gly Gln Pro Phe Glu Val Leu Ile Ile Ala Ser Asp Asp
            85                  90                  95

Gly Phe Lys Ala Val Val Gly Asp Ala Gln Tyr His His Phe Arg His
            100                 105                 110

Arg Leu Pro Leu Ala Arg Val Arg Leu Val Glu Val Gly Gly Asp Val
        115                 120                 125

Gln Leu Asp Ser Val Arg Ile Phe
```

```
                130                 135

<210> SEQ ID NO 3
<211> LENGTH: 139
<212> TYPE: PRT
<213> ORGANISM: Homo sapiens

<400> SEQUENCE: 3

Pro Gly Leu Val Ala Leu Asn Leu Gly Leu Lys Pro Gly Lys Thr Leu
1               5                   10                  15

Thr Val Lys Gly Thr Val Ala Pro Lys Asn Ala Lys Arg Phe Ala Val
            20                  25                  30

Asn Leu Gly Lys Gly Ser Lys Glu Glu Asn Asp Leu Val Leu His Phe
        35                  40                  45

Asn Pro Arg Phe Asn Glu Ala His Gly Asp Gln Asn Thr Val Val Cys
    50                  55                  60

Asn Ser Lys Glu Asn Gly Asp Asn Glu Trp Gly Thr Glu Gln Arg Glu
65                  70                  75                  80

Ala Ala Phe Pro Phe Gln Ala Gly Gln Pro Phe Glu Ile Ser Ile Ser
                85                  90                  95

Val Glu Glu Asp Lys Phe Lys Val Lys Val Asn Asp Gly His Glu Phe
            100                 105                 110

Glu Phe Pro His Arg Leu Lys Leu Glu Ala Val Gln Tyr Leu Gly Ile
        115                 120                 125

Lys Gly Asp Ile Lys Leu Thr Ser Ile Lys Phe
    130                 135

<210> SEQ ID NO 4
<211> LENGTH: 317
<212> TYPE: PRT
<213> ORGANISM: Homo sapiens

<400> SEQUENCE: 4

Met Met Leu Ser Leu Asn Asn Leu Gln Asn Ile Ile Tyr Asn Pro Val
1               5                   10                  15

Ile Pro Phe Val Gly Thr Ile Pro Asp Gln Leu Asp Pro Gly Thr Leu
            20                  25                  30

Ile Val Ile Arg Gly His Val Pro Ser Asp Ala Asp Arg Phe Gln Val
        35                  40                  45

Asp Leu Gln Asn Gly Ser Ser Met Lys Pro Arg Ala Asp Val Ala Phe
    50                  55                  60

His Phe Asn Pro Arg Phe Lys Arg Ala Gly Cys Ile Val Cys Asn Thr
65                  70                  75                  80

Leu Ile Asn Glu Lys Trp Gly Arg Glu Glu Ile Thr Tyr Asp Thr Pro
                85                  90                  95

Phe Lys Arg Glu Lys Ser Phe Glu Ile Val Ile Met Val Leu Lys Asp
            100                 105                 110

Lys Phe Gln Val Ala Val Asn Gly Lys His Thr Leu Leu Tyr Gly His
        115                 120                 125

Arg Ile Gly Pro Glu Lys Ile Asp Thr Leu Gly Ile Tyr Gly Lys Val
    130                 135                 140

Asn Ile His Ser Ile Gly Phe Ser Phe Ser Ser Asp Leu Gln Ser Thr
145                 150                 155                 160

Gln Ala Ser Ser Leu Glu Leu Thr Glu Ile Ser Arg Glu Asn Val Pro
                165                 170                 175

Lys Ser Gly Thr Pro Gln Leu Arg Leu Pro Phe Ala Ala Arg Leu Asn
```

```
                    180                 185                 190
Thr Pro Met Gly Pro Gly Arg Thr Val Val Lys Gly Glu Val Asn
                195                 200                 205
Ala Asn Ala Lys Ser Phe Asn Val Asp Leu Leu Ala Gly Lys Ser Lys
    210                 215                 220
Asp Ile Ala Leu His Leu Asn Pro Arg Leu Asn Ile Lys Ala Phe Val
225                 230                 235                 240
Arg Asn Ser Phe Leu Gln Glu Ser Trp Gly Glu Glu Arg Asn Ile
                245                 250                 255
Thr Ser Phe Pro Phe Ser Pro Gly Met Tyr Phe Glu Met Ile Ile Tyr
                260                 265                 270
Cys Asp Val Arg Glu Phe Lys Val Ala Val Asn Gly Val His Ser Leu
                275                 280                 285
Glu Tyr Lys His Arg Phe Lys Glu Leu Ser Ser Ile Asp Thr Leu Glu
                290                 295                 300
Ile Asn Gly Asp Ile His Leu Leu Glu Val Arg Ser Trp
305                 310                 315

<210> SEQ ID NO 5
<211> LENGTH: 359
<212> TYPE: PRT
<213> ORGANISM: Homo sapiens

<400> SEQUENCE: 5

Met Met Leu Ser Leu Asn Asn Leu Gln Asn Ile Ile Tyr Ser Pro Val
1               5                   10                  15
Ile Pro Tyr Val Gly Thr Ile Pro Asp Gln Leu Asp Pro Gly Thr Leu
                20                  25                  30
Ile Val Ile Cys Gly His Val Pro Ser Asp Ala Asp Arg Phe Gln Val
            35                  40                  45
Asp Leu Gln Asn Gly Ser Ser Val Lys Pro Arg Ala Asp Val Ala Phe
50                  55                  60
His Phe Asn Pro Arg Phe Lys Arg Ala Gly Cys Ile Val Cys Asn Thr
65                  70                  75                  80
Leu Ile Asn Glu Lys Trp Gly Arg Glu Glu Ile Thr Tyr Asp Thr Pro
                85                  90                  95
Phe Lys Arg Glu Lys Ser Phe Glu Ile Val Ile Met Val Leu Lys Asp
                100                 105                 110
Lys Phe Gln Val Ala Val Asn Gly Lys His Thr Leu Leu Tyr Gly His
            115                 120                 125
Arg Ile Gly Pro Glu Lys Ile Asp Thr Leu Gly Ile Tyr Gly Lys Val
    130                 135                 140
Asn Ile His Ser Ile Gly Phe Ser Phe Ser Ser Asp Leu Gln Ser Thr
145                 150                 155                 160
Gln Ala Ser Ser Leu Glu Leu Thr Glu Ile Ser Arg Glu Asn Val Pro
                165                 170                 175
Lys Ser Gly Thr Pro Gln Leu Pro Ser Asn Arg Gly Gly Asp Ile Ser
                180                 185                 190
Lys Ile Ala Pro Arg Thr Val Tyr Thr Lys Ser Lys Asp Ser Thr Val
            195                 200                 205
Asn His Thr Leu Thr Cys Thr Lys Ile Pro Pro Thr Asn Tyr Val Ser
    210                 215                 220
Lys Ile Leu Pro Phe Ala Ala Arg Leu Asn Thr Pro Met Gly Pro Gly
225                 230                 235                 240
```

```
Gly Thr Val Val Val Lys Gly Glu Val Asn Ala Asn Ala Lys Ser Phe
                245                 250                 255

Asn Val Asp Leu Leu Ala Gly Lys Ser Lys His Ile Ala Leu His Leu
                260                 265                 270

Asn Pro Arg Leu Asn Ile Lys Ala Phe Val Arg Asn Ser Phe Leu Gln
                275                 280                 285

Glu Ser Trp Gly Glu Glu Glu Arg Asn Ile Thr Ser Phe Pro Phe Ser
        290                 295                 300

Pro Gly Met Tyr Phe Glu Met Ile Ile Tyr Cys Asp Val Arg Glu Phe
305                 310                 315                 320

Lys Val Ala Val Asn Gly Val His Ser Leu Glu Tyr Lys His Arg Phe
                325                 330                 335

Lys Glu Leu Ser Ser Ile Asp Thr Leu Glu Ile Asn Gly Asp Ile His
                340                 345                 350

Leu Leu Glu Val Arg Ser Trp
        355

<210> SEQ ID NO 6
<211> LENGTH: 135
<212> TYPE: PRT
<213> ORGANISM: Homo sapiens

<400> SEQUENCE: 6

Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
                20                  25                  30

Leu Asn Leu Gly Lys Asp Ser Asn Asn Leu Cys Leu His Phe Asn Pro
            35                  40                  45

Arg Phe Asn Ala His Gly Asp Ala Asn Thr Ile Val Cys Asn Ser Lys
        50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Cys Ile Thr Phe Asp Gln Ala Asn
                85                  90                  95

Leu Thr Val Lys Leu Pro Asp Gly Tyr Glu Phe Lys Phe Pro Asn Arg
                100                 105                 110

Leu Asn Leu Glu Ala Ile Asn Tyr Met Ala Ala Asp Gly Asp Phe Lys
            115                 120                 125

Ile Lys Cys Val Ala Phe Asp
        130                 135
```

COMPOSITIONS AND USES OF A GALECTIN FOR TREATMENT OF DRY EYE SYNDROME

RELATED APPLICATIONS

This application claims the benefit of U.S. provisional patent application Ser. No. 60/562,030, filed Apr. 13, 2004, and U.S. provisional patent application Ser. No. 60/634,361, filed Dec. 8, 2004, the contents of both of which are incorporated herein by reference in their entireties.

GOVERNMENT FUNDING

This invention was made with Government support under grant number EY-07088 from the National Institutes of Health. Accordingly, the government may have certain rights in this invention.

FIELD OF THE INVENTION

Compositions, methods and kits for treatment of dry eye syndrome with a galectin protein are provided.

BACKGROUND OF THE INVENTION

Dry Eye Syndrome (DES) is a common condition that affects up to 10% of the population between the ages of 30 and 45 years, increasing up to 20% of the population 45 years and older (Schein et al., 1997, Am J Ophthamol 124,723–72; Brewitt and Sistani, 2001, Surv of Ophthalmol 45:S119–S202). DES produces ocular irritation, blurred and fluctuating vision and increases the risk of sight-threatening corneal infection and ulceration. The histological effects of DES can include abnormal proliferation and differentiation of the ocular surface epithelium with decreased density of conjunctival goblet cells and decreased and abnormal production of mucus by the ocular surface epithelium (Murillo-Lopez and Pflugfelder, 1996, Dry Eye. In: Krachmer J, Mannis M, Holland E, eds. *The Cornea*. Mosby, St. Louis, Mo. 663–686; Dursun et al., 2002, Invest Ophthamol & Vis Sci 43:632–638). Dry eye disease is a chronic disease, the symptoms and signs of which are greatly influenced by environmental factors, such as humidity and air movement, as well as the demands of certain visual tasks, such as reading or use of a computer.

Typical symptoms of DES are burning, itching, foreign body sensation, stinging, dryness, photophobia, ocular fatigue, and redness. Dry eye disease is a chronic disease, the symptoms and signs of which are greatly influenced by environmental factors, such as humidity and air movement, as well as the demands of certain visual tasks, such as reading or use of a computer (Rheinstrom, 1999, Dry eye. In Yanoff, ed. *Ophthalmology*. 1$^{st}$ Ed. Editor. Mosley International Ltd, St Louis, Mo.; Foulks, 2003, The Ocular Surface, 1: 20–30).

Although a wide variety of artificial tear products are available, all of them provide only transitory relief of symptoms. At present no remedy exists to reverse the condition. Accordingly, there is a need in the art for additional pharmaceutical agents and compositions that treat dry eye syndrome. In particular, there is a need for agents, compositions and therapeutic methods.

SUMMARY OF THE INVENTION

The present invention features a method for treating dry eye in a mammal in need thereof, comprising administering to the mammal a therapeutically effective amount of a galectin protein. An embodiment of the invention is a method for preventing dry eye in a mammal, comprising identifying the mammal in need of preventing dry eye, and administering to the mammal a therapeutically effective amount of a galectin protein. Accordingly, the method is uesed for the mammal in need of treating or preventing selected from the group of mammals having at least one of: ocular epithelial wounds; prior usage of anti-histamine agents; prior usage of anti-inflammatory agents; and prior usage of excimer laser treatment. For example, the mammal is a human. Further, the galectin protein is selected from galectin-8, galectin-7 and galectin-3. In certain embodiments, the dry eye is a persistent syndrome. For example, the dry eye results in epithelial erosion. Further, the epithelial erosion produces a corneal wound.

In general, the galectin-8 protein as used in the above methods comprises the amino acid sequence of SEQ ID NO: 4 or 5. For example, the galectin-8 protein includes an amino acid sequence that is substantially identical to the amino acid sequence of SEQ ID NO: 4 or 5. As used herein, the term "substantially identical" means that the galectin-8 has at least 60% identity, or at least 70% identity, at least 80% identity, or at least 90% identity to the amino acid sequence of SEQ ID NO: 4 or 5.

In general, the galectin-7 protein as used in the above methods includes the amino acid sequence of SEQ ID NO: 2. For example, the galectin-7 protein includes an amino acid sequence that is substantially identical to the amino acid sequence of SEQ ID NO:2. The galectin-7 protein has at least 60% identity, or at least 70% identity, at least 80% identity, or at least 90% identity to the amino acid sequence of SEQ ID NO: 2. In certain embodiments, the galectin-7 protein includes a galectin-7 galactoside-binding domain.

In general, the galectin-3 protein as used in the above methods includes the amino acid sequence of SEQ ID NO: 1. For example, the galectin-3 protein includes an amino acid sequence that is substantially identical to the amino acid sequence of SEQ ID NO: 1. The galectin-3 protein has at least 60% identity, or at least 70% identity, at least 80% identity, or at least 90% identity to the amino acid sequence of SEQ ID NO: 1. In certain embodiments, the galectin-3 protein includes a galectin-3 galactoside-binding domain.

Another embodiment of the invention herein is a pharmaceutical composition having a promoting effect on treatment of dry eye, the composition comprising a pharmaceutically suitable carrier or diluent and an amount of a galectin-8 protein sufficient to promote integrity of conjunctival and/or corneal epithelia. Another embodiment of the invention herein is a pharmaceutical composition having a promoting effect on treatment of dry eye, the composition comprising a pharmaceutically suitable carrier or diluent and an amount of a galectin-7 protein sufficient to promote integrity of conjunctival and/or corneal epithelia. Another embodiment of the invention herein is a pharmaceutical composition having a promoting effect on treatment of dry eye, the composition comprising a pharmaceutically suitable carrier or diluent and an amount of a galectin-3 protein sufficient to promote integrity of conjunctival and/or corneal epithelia. Another embodiment of the invention herein is a pharmaceutical composition having a promoting effect on treatment of dry eye, the composition comprising a pharmaceutically suitable carrier or diluent and an amount of a galectin-8 protein sufficient to promote integrity of conjunctival and/or corneal epithelia. In any of these pharmaceutical compositions, the dry eye is dry eye disease with recurrent epithelial erosion. For example, the dry eye disease produces a wound that is a corneal wound. Further, the dry eye is caused by excimer laser keratectomy.

In various embodiments of the pharmaceutical composition, the galectin-8 protein includes the amino acid sequence of SEQ ID NO: 4 or 5, or the galectin-8 protein includes an amino acid sequence that is substantially identical to the amino acid sequence of SEQ ID NO: 4 or 5. Alternatively, the galectin-8 protein includes a galectin-8 N-terminal domain and a galectin-8 proline, glycine, and tyrosine-rich domain. Alternatively, the galectin-8 protein includes a galectin-8 proline, glycine, and tyrosine-rich domain and a galectin-8 galactoside-binding domain. For example, the galectin-8 protein includes a galectin-8 galactoside-binding domain. Alternatively, the galectin-7 protein includes the amino acid sequence of SEQ ID NO:2. For example, the galectin-7 protein includes an amino acid sequence that is substantially identical to the amino acid sequence of SEQ ID NO: 2. Alternatively, the galectin-7 protein includes a galectin-7 galactoside-binding domain. Alternatively, the galectin-3 protein includes the amino acid sequence of SEQ ID NO: 1. For example, the galectin-3 protein includes an amino acid sequence that is substantially identical to the amino acid sequence of SEQ ID NO:1. For example, the galectin-3 protein includes a galectin-3 galactoside-binding domain.

The invention further features methods for treating dry eye disease in a mammal in need thereof, comprising administering to a mammal a therapeutically effective amount of a substance that influences the spreading of tear film onto the corneal surface or conjunctival surface. The invention also features methods for treating dry eye disease in a mammal in need thereof, comprising administering to a mammal afflicted with a dry eye a therapeutically effective amount of a substance that influences the expression of a galectin-8 protein. For example, the substance comprises a galectin-8 protein with the amino acid sequence of SEQ ID NO:4 or 5. For example, the substance includes a galectin-8 protein with an amino acid sequence that is substantially identical to the amino acid sequence of SEQ ID NO: 4 or 5.

BRIEF DESCRIPTION OF THE DRAWINGS

FIG. 1 depicts the amino acid sequence and composition of human galectin-3 (Accession No. BAA22164 in GenBank, SEQ ID NO: 1).

FIG. 2 depicts the amino acid sequence and composition of human galectin-7 (Accession No. 155469 in GenBank, SEQ ID NO: 2).

FIG. 3 depicts a CLUSTAL W alignment of the amino acid sequence of human galectin-3 (SEQ ID NO: 1) with the amino acid sequences of rabbit galectin-3 (Accession No. JC4300 in GenBank), chicken galectin-3 (Accession No. AAB02856 in GenBank), and hamster galectin-3 (Accession No. CAA55479 in GenBank). The first (upper) sequence in the figure is amino acids 1 to 250 of human galectin-3 (SEQ ID NO: 1), the second sequence in the figure is amino acids 1 to 245 of hamster galectin-3, the third sequence in the figure is amino acids 1 to 242 of rabbit galectin-3, and the fourth (lower) sequence in the figure is amino acids 1 to 262 of chicken galectin-3.

FIG. 4 depicts a CLUSTAL W alignment of the amino acid sequence of human galectin-7 (SEQ ID NO: 2) with the amino acid sequences of rat galectin-7 (Accession No. P97590 in GenBank) and mouse galectin-7 (Accession No. 054974 in GenBank). The first (upper) sequence in the figure is amino acids 1 to 136 of rat galectin-7, the second sequence in the figure is amino acids 1 to 136 of mouse galectin-7, and the third (lower) sequence in the figure is amino acids 1 to 136 of human galectin-7 (SEQ ID NO: 2).

FIG. 5 is a summary of the results of a PROSITE scan of human galectin-3 (SEQ ID NO: 1).

FIG. 6 is a summary of the results of a PROSITE scan of human galectin-7 (SEQ ID NO: 2).

FIG. 7 depicts an alignment of the galactoside-binding domain of human galectin-3 with a consensus amino acid sequence (PF00337) derived from a hidden Markov model (HMM) from PFAM. The upper sequence is the consensus amino acid sequence (PF00337, SEQ ID NO: 3), while the lower amino acid sequence corresponds to amino acids 117 to 247 of SEQ ID NO: 1.

FIG. 8 depicts an alignment of the galactoside-binding domain of human galectin-7 with a consensus amino acid sequence (PF00337) derived from a hidden Markov model (HMM) from PFAM. The upper sequence is the consensus amino acid sequence (PF00337, SEQ ID NO: 3), while the lower amino acid sequence corresponds to amino acids 5 to 135 of SEQ ID NO: 2.

FIG. 9 includes a series of photographs of corneas with 2 mm abrasion or excimer laser wounds that were allowed to partially heal in vivo and were then analyzed for galectin-3 immunoreactivity in paraffin sections. (A), Hematoxylin and eosin staining of (i) normal corneas and corneas immediately after (ii) abrasion and (iii) excimer laser injury. (B), Immunohistochemical staining of (i) normal gal3$^{+/+}$ corneas and (ii) healing gal3$^{+/+}$ corneas after excimer laser injury. Immunohistochemical staining of (iii) normal gal3$^{-/-}$ corneas and (iv) healing gal3$^{-/-}$ corneas after excimer laser injury. Dark color indicates positive immunostaining. WE, wound edge; LE, leading edge of migrating epithelium; arrows, epithelium; arrowheads, leukocytes/stromal cells.

FIG. 14 is a graph illustrating the effect of exogenous galectin-3 on the healing rate of injured corneal epithelium in (FIG. 14A) galectin-3 deficient (gal-3$^{-/-}$) mice and (FIG. 14B) wild type (gal-3$^{+/+}$) mice.

FIG. 16 includes (A) a graph illustrating the effect of exogenous galectin-7 on the healing rate of injured corneal epithelium in wild type (gal-3$^{+/+}$), when used alone, with β-lactose (Lac), or with sucrose (Suc); and (B) a graph comparing the effect of exogenous galectin-7 on the healing rate of injured corneal epithelium in wild type (gal-3$^{+/+}$) and galectin-3 deficient (gal-3$^{-/-}$) mice.

FIG. 17 depicts the amino acid sequence of human galectin-1 (SEQ ID NO: 6).

FIG. 18 depicts the amino acid sequence of the short form of human galectin-8 (SEQ ID NO: 4).

FIG. 19 shows the amino acid sequences of each of human galectin-1 (SEQ ID NO: 6), rat galectin-1, mouse galectin-1 and hamster galectin-1 and that these share a very high percentage of identity, so that galectin-1 sequences are strongly conserved among mammalian species. The shading shows positions of residues that are not identical in all four mammalian sequences. Rat and human are 90.4% identical; mouse and human are 88.2% identical; and hamster and human are 91.2% identical. The figure also shows that the majority of residues at positions that are non-identical are conservative changes, for example, arginine substituted for lysine at position 19, leucine for valine at position 24, serine for threonine at position 73, and aspartic acid for glutamic acid at position 136.

FIG. 20 shows the amino acid sequences of each of the short form (316 amino acid) of human galectin-8 (SEQ ID NO: 4), and corresponding amino acid sequences of short forms of mouse galectin-8, rat galectin-8, chicken galectin-8 and frog galactin-8, aligned with underscoring to indicate gaps in the non-human amino acid sequences compared to the sequence of the human rat galectin-8. The three mammalian galectin-8 amino acid sequences share a very high percentage of identity, and are 78.2% identical with most of the 21.8% non-identities being conserved amino acid changes, such as phenylalanine at position 20 of human compared to tyrosine at the comparable positions in mouse and rat; glycine at position 22 in human and serine in rat; glycine at position 26 of human and aspartate in rodent sequences. Further, the vertebrate species share substantial identity, 43.0%, so that galectin-8 sequences are highly identical among mammalian species and strongly conserved both among vertebrate species.

DESCRIPTION OF SPECIFIC EMBODIMENTS

Figure 10:
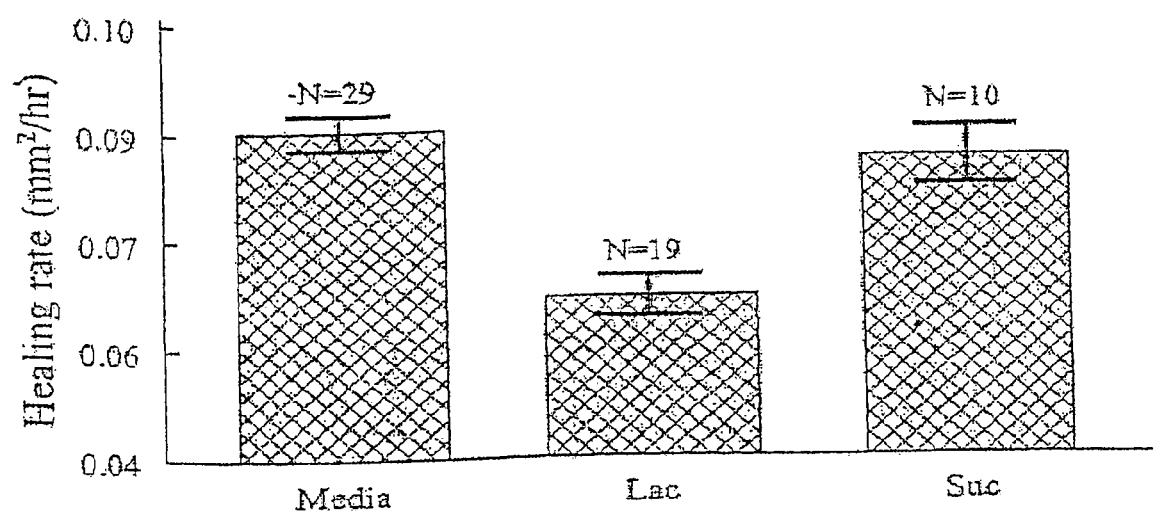
FIG. 10 is a graph illustrating the effect of β-lactose (Lac) and sucrose (Suc) on the healing rate of injured corneal epithelium.

The present application mentions various patents, scientific articles, and other publications. The contents of each such item are hereby incorporated by reference. In addition, the contents (as of the filing date of the application) of all websites referred to herein are incorporated by reference.

Here is presented embodiments of an invention based on the concept that carbohydrate-binding proteins, galectins, can promote the spreading of tear film onto a corneal and conjunctival surface. Galectins are galactose-binding proteins and they bind with high affinity to Galβ1-4GlcNAC disaccharides found in the O-linked oligosaccharides of mucins. Since many galectins are di- or multi-valent, they can promote tear film spreading by binding to oligosaccharides chains of the secretory mucins to the transmembrane mucins (or other glycoproteins) which are present on the apical surface of epithelia of the cornea and the conjunctiva.

The present invention provides pharmaceutical compositions comprising galectin-8, galectin-3 and/or galectin-7 useful for enhancing the re-epithelialization of wounds in injured mammalian tissues. The invention also provides methods for the therapeutic treatment of epithelial injuries in mammalian tissue comprising administering to a mammal afflicted with an epithelial injury a therapeutically effective amount of galectin-1, galectin-3, galectin-7, galectin-8 or a combination of at least two of any of galectins-1, -3, -7 and -8. When administering a combination of galectins-1, -3, -7 and -8, any of the galectins may be administered before, in conjunction with, or after the administration of other galectins.

The invention encompasses the finding that galectin-3 is up-regulated in migrating corneal epithelial cells following injury to the cornea (Example 1). The invention also includes the discovery that the re-epithelialization of corneal transepithelial excimer laser wounds and corneal alkali-burn wounds is significantly slower in galectin-3-deficient mice compared to that in wild type mice (Example 2). The invention further provides the discovery that the expression of a number of injury-related genes (e.g., tolloid-like protein and galectin-7) are abnormal in galectin-3-deficient mice (Example 3). Additionally, the invention demonstrates that exogenous galectin-3 and -7 promote the re-epithelialization of corneal wounds (Examples 4 and 5, respectively).

Galectins

Lectins are proteins that are defined by their ability to bind carbohydrates specifically and to agglutinate cells (see, for example, Sharon, *Trends Biochem. Sci.* 18: 221, 1993). Lectins have been shown to be involved in a wide variety of cellular functions including cell-cell and cell-matrix interactions. Lectins are widespread among plants, invertebrates and mammals. Animal lectins have been grouped into four distinct families: 1) C-type lectins; 2) P-type lectins; 3) galectins (formerly termed S-type lectins); and 4) pentraxins (see, for example, Barondes et al., *J. Biol. Chem.* 269:20807, 1994).

All mammalian galectins that have been analyzed in detail recognize β-lactose and related β-galactosides. While all mammalian galectins share similar affinity for small β-galactosides, they show significant differences in binding specificity for more complex glycoconjugates (Henrick et al., *Glycobiology* 8:45, 1998; Sato et al., *J. Biol. Chem.* 267:6983, 1992; and Seetharaman et al., *J. Biol. Chem.* 273:13047, 1998). In addition to binding β-galactoside sugars, galectins possess hemagglutination activity. Laminin, a naturally occurring glycoprotein containing numerous polylactosamine chains, has been shown to be a natural ligand for certain galectins. Laminin is a component of the basal laminae, the extracellular matrix which underlies all epithelia and surrounds individual muscle, fat and Schwann cells. Interactions between cells and the basal laminae are known to influence the migration and/or differentiation of various cell types during mammalian development. Galectins do not contain traditional sequences that specify membrane translocation, but are both secreted and located intracellularly. In addition to their affinity for β-galactoside sugars, members of the galectin family share significant sequence similarity in the carbohydrate recognition domain (CRD; also referred to as the carbohydrate-binding domain), the relevant amino acid residues of which have been determined by X-ray crystallography (Lobsanov et al., *J. Biol. Chem.* 267:27034, 1993 and Seetharaman et al., supra). Galectins have been implicated in a wide variety of biological functions including cell adhesion (Cooper et al., *J. Cell Biol.* 115:1437, 1991), growth regulation (Wells et al., *Cell* 64:91, 1991), cell migration (Hughes, *Curr. Opin. Struct. Biol.* 2:687, 1992), neoplastic transformation (Raz et al., *Int. J. Cancer* 46:871, 1990) and immune responses (Offner et al., *J. Neuroimmunol.* 28:177, 1990). There are presently 12 characterized eukaryotic members of the galectin family.

Galectin-3

Members of the galectin-3 family of proteins (previously known as CBP-35, Mac-2, L-34, εBP, and RL-29) typically include between about 240 and 270 amino acids and have molecular weights that range between about 25 and 29 kDa. Galectin-3 proteins are generally composed of a short N-terminal domain, a C-terminal domain which includes a galactoside-binding region, and an intervening proline, glycine, and tyrosine-rich domain which includes repeats of 7–10 conserved amino acids (Liu et al., *Biochemistry* 35:6073, 1996 and Cherayil et al., *Proc. Natl. Acad. Sci. USA,* 87:7324, 1990). The tandem repeats are similar to those found in the collagen gene superfamily. The number of repeats varies between galectin-3 proteins and accounts for the differences in size between galectin-3 proteins from different species. The N-terminal domain of galectin-3 permits the protein to undergo multimerization upon binding to surfaces containing glycoconjugate ligands.

Galectin-3 is expressed in various inflammatory cells (e.g., activated macrophages, basophils, and mast cells) and in epithelia and fibroblasts of various tissues (Perillo et al., *J. Mol. Med.* 76:402, 1998). It is found on the cell surface, within the extracellular matrix (ECM), in the cytoplasm, and in the nucleus of cells. On the cell surface or in the ECM galectin-3 is thought to mediate cell-cell and cell-matrix interactions by binding to complementary glycoconjugates containing polylactosamine chains found in many ECM and cell surface molecules. Galectin-3 is thought to inhibit cell-matrix adhesion by binding to laminin. In the nucleus of cells galectin-3 may influence cell-matrix interactions indirectly by influencing the expression of well-known cell adhesion molecules (e.g., α6β1 and α4β7 integrins, Warlfield et al., *Invasion Metastasis* 17:101, 1997 and Matarrese et al., *Int. J. Cancer* 85:545, 2000) and cytokines (e.g., IL-1, Jeng et al., *Immunol. Lett.* 42: 113, 1994). Galectin-3 expression is developmentally regulated in selected organs such as the kidney and its expression level in pulmonary alveolar epithelial cells and hepatocytes is up-regulated following injury. Galectin-3 has been shown to concentrate in the nucleus of certain cell types during proliferation. Expression of galectin-3 is elevated in certain tumors, suggesting galectin-3 plays a role in metastasis. Indeed, overexpression of galectin-3 in a weakly metastatic cell line caused a significant increase in metastatic potential (Raz et al., supra).

Human galectin-3 is 250 amino acids long and has an approximate molecular weight of 26.1 kDa (SEQ ID NO: 1, FIG. 1). As illustrated in FIGS. 1, 3, 5, and 7, human galectin-3 contains the following domains, signature sequences, or other structural features (for general information regarding PS and PF prefix identification numbers, refer to Sonnhammer et al., *Protein* 28:405, 1997): an N-terminal domain located at about amino acid residues 1 to 14 of SEQ ID NO: 1; a proline, glycine, and tyrosine-rich domain located at about amino acid residues 15 to 116 of SEQ ID NO: 1; a galactoside-binding domain located at about amino acid residues 117 to 247 of SEQ ID NO: 1; a galaptin signature sequence (PROSITE No. PS00309) located at about amino acids 181 to 200 of SEQ ID NO: 1; one potential N-glycosylation site (PROSITE No. PS00001) located at about amino acids 4 to 7 of SEQ ID NO: 1; two potential protein kinase C phosphorylation sites (PROSITE No. PS00005) located at about amino acids 137 to 139 and 194 to 196 of SEQ ID NO: 1; two potential casein kinase II phosphorylation sites (PROSITE No. PS00006) located at about amino acids 6 to 9 and 175 to 178 of SEQ ID NO: 1; and eight potential myristoylation sites (PROSITE No. PS00008) located at about amino acids 24 to 29, 27 to 32, 34 to 39, 43 to 48, 52 to 57, 61 to 66, 65 to 70, and 68 to 73 of SEQ ID NO: 1.

As defined herein, a "galectin-3 protein" may include a galectin-3 "N-terminal domain", a galectin-3 "proline, glycine, and tyrosine-rich domain", and/or a galectin-3 "galactoside-binding domain". These domains are further defined as follows.

As used herein, a galectin-3 "N-terminal domain" includes an amino acid sequence of about 10–20 amino acids, preferably about 14 amino acids that shares at least about 60%, 70%, 80%, 90%, 95%, 99%, or 100% identity with amino acids 1 to 14 of SEQ ID NO: 1. The N-terminal domain can include an N-glycosylation site (PROSITE No. PS00001) and/or a casein kinase II phosphorylation site (PROSITE No. PS00006). The PROSITE N-glycosylation site has the consensus sequence: N-{P}-[ST]-{P} and the PROSITE casein kinase II phosphorylation site has the consensus sequence: [ST]-X(2)-[DE]. In the above consensus sequences, and other motifs or signature sequences described herein, the standard IUPAC one-letter code for the amino acids is used. Each element in the pattern is separated by a dash (–); square brackets ([ ]) indicate the particular residues that are accepted at that position; X indicates that any residue is accepted at that position; and numbers in parentheses (( )) indicate the number of residues represented by the accompanying amino acid. In certain embodiments, the N-terminal domain includes amino acids L7 and L11 of SEQ ID NO: 1. As shown in FIG. 3, these amino acids are conserved across several mammalian species of galectin-3 and may therefore play a catalytic and/or structural role.

As used herein, a galectin-3 "proline, glycine, and tyrosine-rich domain" includes an amino acid sequence of about 60 to 140 amino acids, more preferably about 80 to 120 amino acids, or about 90 to 110 amino acids that shares at least about 60%, 70%, 80%, 90%, 95%, 99%, or 100% identity with amino acids 15 to 116 of SEQ ID NO: 1. The proline, glycine, and tyrosine-rich domain can also include one, two, three, four, five, six, seven, or eight N-myristoylation sites (PROSITE No. PS00008) which have the consensus sequence: G-{EDRKHPFYW}-X(2)-[STAGCN]-{P}. In certain embodiments, the proline, glycine, and tyrosine-rich domain includes the following amino acids and regions of SEQ ID NO: 1: G21, P23, G27, N28, P30, G32, G34, P37, Y41-P46, G53, Y55-G57, P61, G62, G66, P72, G73, G77, Y79-G81, P83, G87, Y89, P90, G99, Y101, P102, P106, Y107, A109, L114, and V116. These amino acids and regions are conserved across several mammalian species of galectin-3 and may play a catalytic and/or structural role (see amino acids indicated with a "*" in FIG. 3).

As used herein, a galectin-3 "galactoside-binding domain" includes an amino acid sequence of about 80 to 180 amino acids having a bit score for the alignment of the sequence to the consensus sequence PF00337 from PFAM (ID NO: 3) of at least 150. Preferably, a galectin-3 galactoside-binding domain includes at least about 100 to 160 amino acids, more preferably about 110 to 150 amino acids, or about 120 to 140 amino acids and has a bit score for the alignment of the sequence to the consensus sequence PF00337 from PFAM (SEQ ID NO: 3) of at least 150, more preferably at least 175, most preferably 200 or greater.

To calculate the bit score for the alignment of a particular sequence to the consensus sequence PF00337 from PFAM, the sequence of interest can be searched against the PFAM database of HMMs (e.g., the PFAM database, release 2.1) using the default parameters available at www.sanger.ac.uk/Software/Pfam. A description of the PFAM database can be found in Sonnhammer et al., supra and a detailed description of HMMs can be found, for example, in Gribskov et al., Meth. Enzymol. 183:146, 1990 and Stultz et al., Protein Sci. 2:305, 1993.

The galectin-3 galactoside-binding domain can further include one, preferably two, protein kinase C phosphorylation sites (PROSITE No. PS00005); a casein kinase II phosphorylation site (PROSITE No. PS00006); and/or a galaptin signature sequence (PROSITE No. PS00309). The protein kinase C phosphorylation site has the following consensus sequence: [ST]-X-[RK]. The galaptin signature sequence has the following consensus sequence: W-[GEK]-X-[EQ]-X-[KRE]-X(3,6)-[PCTF]-[LIVMF]-[NQEGSKV]-X-[GH]-X(3)-[DENKHS]-[LIVMFC]. In certain embodiments, the galectin-3 galactoside-binding domain includes the following amino acids and regions of ID NO: 1: P117, Y118, L120-L122, G125, P128, R129, L131–L134, G136-V138, N141, N143, R144, L147, F149, R151, G152, D154, A156-F163, E165, R169-N174, N179-G182, E184-R186, F190-E193, G195, P197-K199, Q201-L203, E205, D207-Q220, N222, R224, L228, I231, I236, G238-I240, and L242-S244. These amino acids and regions are conserved across several mammalian species of galectin-3 and may play a catalytic and/or structural role (see amino acids indicated with a "*" in FIG. 3).

Certain galectin-3 proteins of the present invention include the amino acid sequence of human galectin-3 as represented by SEQ ID NO: 1. Other galectin-3 proteins of the present invention include an amino acid sequence that is substantially identical to the amino acid sequence of SEQ ID NO: 1. The term "substantially identical" is used herein to refer to a first amino acid that contains a sufficient or minimum number of amino acid residues that are identical to aligned amino acid residues in a second amino acid sequence such that the first and second amino acid sequences can have a common structural domain and/or common functional activity. For example, amino acid sequences that contain a common structural domain having at least about 60%, or 65% identity, preferably at least 75% identity, more preferably at least 85%, 90%, 91%, 92%, 93%, 94%, 95%, 96%, 97%, 98%, or 99% identity to SEQ ID NO: 1 are termed substantially identical to the amino acid sequence of SEQ ID NO: 1. In particular, proteins which contain accidentally or deliberately induced alterations, such as deletions, additions, substitutions or modifications of certain amino acid residues of SEQ ID NO: 1 may fall within the definition of galectin-3 proteins provided herein. It will also be appreciated that as defined herein, galectin-3 proteins may include regions represented by the amino acid sequence of galectin-3 taken from other mammalian species including but not limited to bovine, canine, feline, caprine, ovine, porcine, murine, and equine species.

Calculations of sequence identity between sequences are performed as follows. To determine the percent identity of two amino acid sequences, the sequences are aligned for optimal comparison purposes (e.g., gaps can be introduced in one or both of a first and a second amino acid sequence for optimal alignment). The amino acid residues at corresponding amino acid positions or nucleotide positions are then compared. When a position in the first sequence is occupied by the same amino acid residue or nucleotide as the corresponding position in the second sequence, then the proteins are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using an alignment software program using the default parameters. Suitable programs include, for example, CLUSTAL W by Thompson et al., Nuc. Acids Research 22:4673, 1994 (www.ebi.ac.uk/clustalw), BL2SEQ by Tatusova and Madden, FEMS Microbiol. Lett. 174:247, 1999 (www.ncbi.nlm.nih.gov/blast/b12seq/b12.html), SAGA by Notredame and Higgins, Nuc. Acids Research 24:1515, 1996 (igs-server.cnrs-mrs.fr/~cnotred), and DIALIGN by Morgenstern et al., Bioinformatics 14:290, 1998 (bibiserv.techfak.uni-bielefeld.de/dialign).

Galectin-7

Members of the galectin-7 family of proteins typically exist as monomers that include between about 130 and 140 amino acids and have molecular weights that range between about 15 and 16 kDa (see, for example, Magnaldo et al., Develop. Biol. 168:259, 1995 and Madsen et al., J. Biol. Chem. 270:5823, 1995). The expression of galectin-7 has been associated with the onset of epithelial stratification (Timmons et al., Int. J. Dev. Biol. 43:229, 1999). Galectin-7 is thought to play a role in cell-matrix and cell-cell interactions. Galectin-7 is found in areas of cell-cell contact (e.g., in the upper layers of human epidermis); its expression is sharply downregulated in anchorage independent keratinocytes and it is absent in a malignant keratinocyte cell line. Galectin-7 may be required for the maintenance of normal keratinocytes (see, Madsen et al., supra).

Human galectin-7 includes 136 amino acids and has an approximate molecular weight of 15.1 kDa (SEQ ID NO: 2, FIG. 2). As illustrated in FIGS. 2, 4, 6, and 8, human galectin-7 contains the following domains, signature sequences, or other structural features: a galactoside-binding domain located at about amino acid residues 5 to 135 of SEQ ID NO: 2; a galaptin signature sequence (PROSITE No. PS00309) located at about amino acids 70 to 89 of SEQ ID NO: 2; one N-glycosylation site (PROSITE No. PS0001) located at about amino acids 29 to 32 of SEQ ID NO: 2; one protein kinase C phosphorylation site (PROSITE No. PS00005) located at about amino acids 132 to 134 of SEQ ID NO: 2; one casein kinase II phosphorylation site (PROSITE No. PS00006) located at about amino acids 9 to 12 of SEQ ID NO:2; and two myristoylation sites (PROSITE No. PS00008) located at about amino acids 13 to 18 and 44 to 49 of SEQ ID NO: 2.

As defined herein, a "galectin-7 protein" includes a galectin-7 "galactoside-binding domain". This domain is further defined as follows.

As used herein, a galectin-7 "galactoside-binding domain" includes an amino acid sequence of about 80 to 180 amino acids having a bit score for the alignment of the sequence to the consensus sequence PF00337 from PFAM (SEQ ID NO: 3) of at least 80. Preferably, a galectin-7 galactoside-binding domain includes at least about 100 to 160 amino acids, more preferably about 110 to 150 amino acids, or about 120 to 140 amino acids and has a bit score for the alignment of the sequence to the consensus sequence PF00337 from PFAM (SEQ ID NO: 3) of at least 80, more preferably at least 100, most preferably 120 or greater. The galectin-7 galactoside-binding domain can include one N-glycosylation site (PROSITE No. PS00001); one protein kinase C phosphorylation site (PROSITE No. PS00005); one casein kinase II phosphorylation site (PROSITE No. PS00006); one or two myristoylation sites (PROSITE No. PS00008); and/or a galaptin signature sequence (PROSITE No. PS00309). In certain embodiments, the galectin-7 galactoside-binding domain includes the following amino acids and regions of SEQ ID NO: 2: M1, S2, H6, K7, L10, P11, G13, R15, G17-V19, R21-G24, V26, P27, A30, R32-Q43, D46-N63, K65, Q67, G68, W70-G76, G78, P80-L90, 192, G97-K99, V101, G103, D104, Y107, H109, F110, H112, R113, P115, V119, R120, V122-L130, S132, I135, and F136. These amino acids and regions are conserved across several mammalian species of galectin-7 and may play a catalytic and/or structural role (see amino acids indicated with a "*" in FIG. 4).

Certain galectin-7 proteins of the present invention include the amino acid sequence of human galectin-7 as represented by SEQ ID NO: 2. Other galectin-7 proteins of the present invention include an amino acid sequence that is substantially identical to the amino acid sequence of SEQ ID NO: 2. In particular, proteins which contain accidentally or deliberately induced alterations, such as deletions, additions, substitutions or modifications of certain amino acid residues of SEQ ID NO: 2 may fall within the definition of galectin-7 provided herein. It will also be appreciated that as defined herein, galectin-7 proteins may include regions represented by the amino acid sequence of galectin-7 taken from other mammalian species including but not limited to bovine, canine, feline, caprine, ovine, porcine, murine, and equine species.

Galectin-8

Galectin-8 is a widely expressed protein, present for example, in liver, heart, muscle, kidney, spleen, hind-limb and brain, and the sequence of human and rat galectin-8 genes and proteins are available (see for example Hadari, et al., Trends in Glycosci and Glycotechnol. 9: 103–112, 1997). The highly hydrophilic character and function for binding to Galβ1-4GlcNAC disaccharides found in the O-linked oligosaccharides of mucins make this protein an ideal agent for treating dry eye syndrome.

Two forms of amino acid sequence for human galectin-8 are known, a 316 amino acid form (Accession number O00214, created 1 Nov. 1997) and a 359 amino acid form (Accession number Q8TEV1, created 1 Jun. 2002). These sequences, while similar or identical for significant lengths, are not overall mere length variants, having portions of difference. The 316 form amino acid sequence, using the one letter amino acid code, is shown below (SEQ ID NO: 4):

```
MLSLNNLQNI IYNPVIPYVG TIPDQLDPGT LIVICGHVPS      60
DADRFQVDLQ NGSSVKPRAD

VAFHFNPRFK RAGCIVCNTL INEKWGREEI TYDTPFKREK     120
SFEIVIMVLK DKFQVAVNGK

HTLLYGHRIG PEKIDTLGIY GKVNIHSIGF SFSSDLQSTQ     180
ASSLELTEIS RENVPKSGTP

QLSLPFAARL NTPMGPGRTV VVKGEVNANA KSFNVDLLAG     240
KSKDIALHLN PRLNIKAFVR

NSFLQESWGE EERNITSFPF SPGMYFEMII YCDVREFKVA     300
VNGVHSLEYK HRFKELSSID

TLEINGDIHL LEVRSW                              316
```

The amino acid sequence of the longer form is shown below (SEQ ID NO: 5):

```
MMLSLNNLQN IIYSPVIPYV GTIPDQLDPG TLIVICGHVP      60
SDADRFQVDL QNGSSVKPRA

DVAFHFNPRF KRAGCIVCNT LINEKWGREE ITYDTPFKRE     120
KSFEIVIMVL KDKFQVAVNG

KHTLLYGHRI GPEKIDTLGI YGKVNIHSIG FSFSSDLQST     180
QASSLELTEI SRENVPKSGT

PQLPSNRGGD ISKIAPRTVY TKSKDSTVNH TLTCTKIPPT     240
NYVSKILPFA ARLNTPMGPG

GTVVVKGEVN ANAKSFNVDL LAGKSKHIAL HLNPRLNIKA     300
FVRNSFLQES WGEEERNITS

FPFSPGMYFE MIIYCDVREF KVAVNGVHSL EYKHRFKELS     359
SIDTLEINGD IHLLEVRSW
```

As defined herein, a "galectin-8 protein" may include a galectin-8 "N-terminal domain", a galectin-8 "proline, glycine, and tyrosine-rich domain", and/or a galectin-8 "galactoside-binding domain". These domains are further defined as follows.

As used herein, a galectin-8 "N-terminal domain" includes an amino acid sequence of about 10–20 amino acids, preferably about 14 amino acids that shares at least about 60%, 70%, 80%, 90%, 95%, 99%, or 100% identity with amino acids 1 to 14 of SEQ ID NOs:4 or 5. The N-terminal domain can include an N-glycosylation site (PROSITE No. PS00001) and/or a casein kinase II phosphorylation site (PROSITE No. PS00006). The PROSITE N-glycosylation site has the consensus sequence: N-{P}-[ST]-{P} and the PROSITE casein kinase II phosphorylation site has the consensus sequence: [ST]-X(2)-[DE]. In the above consensus sequences, and other motifs or signature sequences.

As used herein, a galectin-8 "proline, glycine, and tyrosine-rich domain" includes an amino acid sequence of about 60 to 140 amino acids, more preferably about 80 to 120 amino acids, or about 90 to 110 amino acids that shares at least about 60%, 70%, 80%, 90%, 95%, 99%, or 100% identity with amino acids 15 to 116 of each of SEQ ID NOs: 4 and 5. The proline, glycine, and tyrosine-rich domain can also include one, two, three, four, five, six, seven, or eight N-myristoylation sites (PROSITE No. PS00008) which have the consensus sequence: G-{EDRKHPFYW}-X(2)-[STAGCN]-{P}. In certain embodiments, the proline, glycine, and tyrosine-rich domain includes the following amino acids and regions of SEQ ID NO: 4: G20, P23, P28, G29, G36, P39, and other such residues as are obvious to one of skill in the art. These amino acids and regions are conserved across several mammalian species of galectin-8 and may play a catalytic and/or structural role. In certain embodiments, the proline, glycine, and tyrosine-rich domain includes the following amino acids and regions of SEQ ID NO:5: G21, P24, P29, G30, G37, P40, and other such residues as are obvious to one of skill in the art.

As used herein, a galectin-4 "galactoside-binding domain" includes an amino acid sequence of about 80 to 180 amino acids having a bit score for the alignment of the sequence to the consensus sequence PF00337 from PFAM (SEQ ID NO: 3) of at least 150. Preferably, a galectin-3 galactoside-binding domain includes at least about 100 to 160 amino acids, more preferably about 110 to 150 amino acids, or about 120 to 140 amino acids and has a bit score for the alignment of the sequence to the consensus sequence PF00337 from PFAM (SEQ ID NO: 3) of at least 150, more preferably at least 175, most preferably 200 or greater.

To calculate the bit score for the alignment of a particular sequence to the consensus sequence PF00337 from PFAM, the sequence of interest can be searched against the PFAM database of HMMs (e.g., the PFAM database, release 2.1) using the default parameters available at www.sanger.ac.uk/Software/Pfam. A description of the PFAM database can be found in Sonnhammer et al., supra and a detailed description of HMMs can be found, for example, in Gribskov et al., *Meth. Enzymol.* 183:146, 1990 and Stultz et al., *Protein Sci.* 2:305, 1993.

A galectin-8 galactoside-binding domain can further include one, preferably two, protein kinase C phosphorylation sites (PROSITE No. PS00005); a casein kinase II phosphorylation site (PROSITE No. PS00006); and/or a galaptin signature sequence (PROSITE No. PS00309). The protein kinase C phosphorylation site has the following consensus sequence: [ST]-X-[RK]. The galaptin signature sequence has the following consensus sequence: W-[GEK]-X-[EQ]-X-[KRE]-X(3,6)-[PCTF]-[LIVMF]-[NQEGSKV]-X-[GH]-X(3)-[DENKHS]-[LIVMFC]. In certain embodiments, the galectin-8 galactoside-binding domain includes the following amino acids and regions of SEQ ID NO: 4: L123-L124, G126, P131, R128, L140-I146, and other sites similar to those as demonstrated above. These amino acids and regions are conserved across several mammalian species of galectin-8 and may play a catalytic and/or structural role (see amino acids indicated with a "*" in FIG. 3).

Certain galectin-8 proteins of the present invention include the amino acid sequence of human galectin-8 as represented by SEQ ID NOs: 4 and 5. Other galectin-8 proteins of the present invention include an amino acid sequence that is substantially identical to the amino acid sequence of SEQ ID NOs: 4 or 5. The term "substantially identical" is used herein to refer to a first amino acid that contains a sufficient or minimum number of amino acid residues that are identical to aligned amino acid residues in a second amino acid sequence such that the first and second amino acid sequences can have a common structural domain and/or common functional activity. For example, amino acid sequences that contain a common structural domain having at least about 60%, or 65% identity, preferably at least 75% identity, more preferably at least 85%, 90%, 91%, 92%, 93%, 94%, 95%, 96%, 97%, 98%, or 99% identity to SEQ ID NOs:4 or 5 are termed substantially identical to the amino acid sequence of SEQ ID NOs:4 or 5. In particular, proteins which contain accidentally or deliberately induced alterations, such as deletions, additions, substitutions or modifications of certain amino acid residues of SEQ ID NOs: 4 or 5 may fall within the definition of galectin-8 proteins provided herein. It will also be appreciated that as defined herein, galectin-8 proteins may include regions represented by the amino acid sequence of galectin-8 taken from other mammalian species including but not limited to bovine, canine, feline, caprine, ovine, porcine, murine, and equine species.

Dry eye syndrome is considered the "common cold" of ophthalmology and is the second most common complaint of patients presenting to ophthalmologists. Nearly fifteen million Americans suffer with dry eyes. The disease is caused by a deficiency in either structure or function of the tear film. The tear film is has a dynamic structure and its production and turnover is essential to maintaining the health of the ocular surface. The tear film is composed of three layers: the mucin (innermost), aqueous (middle) and lipid (top) layers. A dysfunction of any of these layers can result in dry eye disease. The tear film is linked to the surface of epithelial cells through the mucin molecules present in the innermost layer. The mucin layer promotes an even spreading of the tear film over the cornea, a necessary requisite for proper ocular surface wetting. If the mucin molecules do not adhere to the eye, epithelial damage may occur even with normal aqueous tear production. Defective spreading of the tear film can disturb the ocular surface or tear film and cause dry eye disease. The inner mucin layer is produced by conjunctival goblet cells and by conjunctival and corneal epithelial cells. Ocular mucins can be either membrane spanning (e.g. MUCI and MUCU), or gel forming/secretory (e.g. MUC5AC).

The mucins are exceptionally large glycoproteins that have at least half of their mass as O-linked carbohydrate. The abundant O-linked carbohydrate side chains are responsible for the very hydrophilic character of mucins. It is thought that it is this hydrophilic property that allows the aqueous layer to spread evenly over the eye.

The present invention is based on therapeutic use of galectins for treatment of Dry Eye Syndrome (DES). Without being limited by any particular mechanism, this use is based on the carbohydrate-binding properties of the galectins. Topically applied galectins in ophthalmic solution will promote tear film spreading by binding secretory mucins to transmembrane mucins or other glycoproteins present on the surface of the conjunctiva and corneal epithelium.

In the examples herein, the effects of topically applied galectin solutions in three different murine models of dry eye will be determined. In one model, tear insufficiency is induced by applying scopolamine patches to the tail of normal mice, according to the method reported by Pflugfelder's Laboratory (Dursun et al., 2002, Invest Ophthamol & Vis Sci. 43:632–638; Pflugfelder et al., 2003, The Ocular Surface, 1:31–36). The second model utilizes MRL/lpr autoimmune mice, which develop lacrimal gland inflammatory lesions, a model which has been proposed for Sjögrens Syndrome (Jabs et al., 1991, Invest Ophthamol Vis Sci. 32:371–380; Jabs et al., 1997, Curr Eye Res. 16:909–916). The third model uses injection of IL-1α to produce an animal model that is equivalent of Sjögrens Syndrome (see (Zoukhri, D. et al., Invest Ophthalmol Vis Sci 42(5): 925–932).

Measurements include in vivo assay of tear production, tear clearance, and corneal fluorescein staining, to determine the effects of various concentrations of galectin-1, galectin-3, galectin-7, and galectin-8 on these parameters, alone or in combination, as compared to control animals treated with vehicle, and following in vivo assays, biochemical assays on isolated lacrimal glands, and histopathology on ocular surface. Further, effects of pre-treatment with galectin solutions prior to scopolomine treatment is examined, as is a possible effect of combined treatment of galectins with β-lactose, a galectin inhibitor.

Data obtained from examples herein show that a galectin produced statistically significant effects on the measurable parameters associated with dry eye syndrome in the model. A decrease in corneal fluorescein staining of corneas in eyes of galectin-treated animals as compared to placebo-treated animals provides strong evidence that galectins have excellent therapeutic potential for human DES. Since the two animal models represent distinct forms of DES, positive results in either model will help determine the role galectins may play in DES treatment, and guide the focus of the clinical trials that include additional animal experiments to determine the optimal concentration of galectin required for maximal beneficial effects, the duration of the effect, and the binding characteristics of galectins to the cornea and to endogenous mucins. Furthermore, toxicity studies are performed to establish a safe ocular dose range and fulfill FDA requirements prior to receiving approval for clinical trials.

The innermost layer of the tears consists of mucin produced from the goblet cells of the conjunctiva and by epithelial cells of the cornea and conjunctiva. The mucins may be released and exist as secretory mucins, or may remain attached to the epithelium as transmembrane mucins. These molecules are glycoproteins that have abundant O-linked carbohydrate side chains. The side chains are responsible for the very hydrophilic character of mucins, which allows the aqueous layer to spread evenly over the eye. The aqueous layer, produced by the lacrimal glands, constitutes about 90% of the tear film. It is comprised mostly of water with dissolved salts, glucose, lysozyme, tear-specific prealbumin, lactoferrin, secretory immunoglobulin A, and other proteins. The outer lipid layer retards evaporation, and is composed of sebaceous material produced from the meibomian glands. Blinking acts to spread this layer over the tear film (Rheinstrom S D, 1999, Dry eye. In Yanoff, ed. *Ophthalmology*. 11t Ed. Editor. Mosley International Ltd, St Louis, Mo.).

The National Eye Institute has classified dry eye conditions into two major categories: aqueous layer deficiency and evaporative deficiency. However, the clinical presentation is often a mix of the two pathogenic pathways (a reduced tear production often results in defective oily layer spreading in excessive evaporation and meibomian gland disease is very often associated with a hyposecretive dry eye). Subcategorization of the aqueous tear deficient group into Sjögren's syndrome dry eye and non-Sjögren's syndrome dry eye recognizes a difference in severity of disease between the two groups and emphasizes the inflammatory expression of Sjögren's syndrome (Foulks, 2003, The Ocular Surface. 1:20–30).

Aqueous layer deficiency is the most common cause of dry eye and is usually caused by decreased tear secretion from the lacrimal glands, although increased evaporation of tears may also be involved. Causes of reduced secretion include Sjögren's syndrome, senile hyposecretion, lacrimal gland excision, vitamin A deficiency, immune lacrimal gland damage in sarcoidosis or lymphoma, sensory or motor reflex loss, scarring conditions of the conjunctiva, and contact lens wear (Rolando and Zierhut, Surv Ophthalmol. 45:S203–S210, 2001). Changes in the composition of the aqueous layer, such as increased electrolyte concentration, loss of growth factors, or presence of pro-inflammatory cytokines, together with a slow tear turnover, are also associated with ocular surface damage.

Goblet cell deficiency, and thus decreased mucin levels, accompanies many forms of dry eye. Certain disorders in particular may precipitate goblet cell loss. These include vitamin A deficiency, as vitamin A is essential for the maintenance of goblet cells and mucin at the ocular surface, and cicatrizing conjunctival disorders, such as Stevens-Johnson syndrome, trachoma, pemphigoid, and chemical burns. Topical medications and preservatives can also damage the ocular surface and goblet cells (Rheinstrom S D, 1999, Dry eye. In Yanoff, ed. *Ophthalmology*. 1$^{st}$ Ed. Editor. Mosley International Ltd, St Louis, Mo.; Abelson et al., 2003, Rev Ophthalmol 10:1).

In addition to evaluation of patient discomfort, diagnostic techniques have proven useful for determining the severity and cause of DES. Tear-film instability can be assessed using non-invasive measurements of tear break-up time (TBUT) in which fluorescein solution is applied, and the time to first breakup of tear film as observed biomicroscopically is measured. Tear production can be estimated using the classic or modified Schirmer test. The degree of ocular surface staining, using fluoresein or similar dyes, is routinely used to diagnose the severity of alteration of the ocular surface. These dyes stain epithelial surfaces that have been deprived of mucin protein protection or have exposed epithelial cell membranes. Standardized grading systems have been developed to quantify the severity of damage. These tests are also routinely used in clinical trials to assess the therapeutic effects of investigative dry eye treatments (Foulks, 2003, The Ocular Surface, 1:20–30).

Artificial tears are the mainstay of current dry eye treatments. A wide variety of commercial products are available, but all of them provide only transitory relief of symptoms. At present no remedy exists to reverse the condition. The addition of higher molecular weight polymers such as cellulose esters (methylcellulose, hydroxypropyl methylcellulose) or polyvinyl alcohol to saline can be used to create artificial tears. Other artificial tear formulations have been prepared in attempts to mimic the mucin component of tears. Studies have shown that the preservatives used in artificial tears can produce some toxicity and, as a result, unit dose vials of artificial tears without preservatives have become available. (Rheinstrom S D, 1999, Dry eye. In Yanoff, ed. *Ophthalmology*. 1$^{st}$ Ed. Editor. Mosley International Ltd, St Louis, Mo.; Abelson, 2003, Rev Ophthalmol 10:1).

With advances in the understanding of the pathophysiology of the disease, many different modalities of therapy have been introduced, including those that target disorders of the lipid layer of the tears and the underlying immunologic or hormonal causes of the disease (Brewitt et al., 2001, Surv of Ophthalmol 45:S119–S202). Investigational therapies include the use of topical secretagogues such as 15(S)-HETE (hydroxy-eicosatetraenoic acid) (Gamache et al., 2000, Cornea 19:6:S88), and a synthetic P2Y2 receptor agonist (Jumblatt et al., 1998, Exp Eye Res 67:341–346), as well as anti-inflammatory agents such as Cyclosporin A, and corticosteroids (Pflugfelder, 2003, The Ocular Surface, 1:31–36).

Mucins are known to have a role in healthy ocular tear film physiology. Mucins are high-molecular weight glycoproteins with a protein backbone and high carbohydrate content. In addition to contributing to the mucus layer, the mucins themselves form the glycocalyx, a scaffold-like structure that helps contribute to cell adhesion. They are also a defense against ocular surface damage. Mucins also serve in making the tear film hydrophilic. This stabilizes the tear film and decreases its surface tension, allowing the aqueous layer to spread evenly over the surface of the eye. Without this layer, tears wouldn't adhere to the surface, making it susceptible to damage. (Abelson et al., 2003, Rev Ophthalmol 10:1).

Two primary types of mucins are produced within the body: membrane spanning mucins and secreted mucins. The membrane-spanning mucins (MUC1, MUC2, and MUC4) are embedded in the lipid bilayer of the cells. The membrane-spanning mucins expressed by the corneal and conjuctival non-goblet cells are thought to help spread the secreted mucins (MUC5AC, MUC7), produced by goblet cells across the ocular surface. The two types of mucin work together to form of a viable tear film (Danjo et al., 1998, Invest Ophthalmol Vis Sci 39: 2602–2609; Watanabe 2002, Cornea 21:S17–S22).

A deficiency in conjunctival mucin plays a role in certain types of dry-eye disorders. Possible causes include a decreased density of goblet cells, alterations in mucin distribution or character, and lowered mucin mRNA expression (Gipson et al., 2000, Prog Retinal Eye Res, 16:1:81–98; Gilbard, 2000, "Dry-eye disorders", In: Albert M et al., eds. *Principals and Practice of Ophthalmology:* $2^{nd}$ Edition, Philadelphia: W.B. Saunders Company: 982–1001). Vitamin A deficiencies, topical medications, excessive dosing with drops containing preservatives and cicatrizing conjunctival disorders can all damage goblet cells and the ocular surface (Danjo et al., 1998, Invest Ophthalmol Vis Sci 39: 2602–2609; Abelson et al., 2003, Rev Ophthalmol 10:1)

Transmembrane mucins found on the ocular surface are also altered in patients with dry eye. Researchers have proposed that the transmembrane mucins, such as MUC1, produced in dry-eye patients are not glycosylated, as are mucins of normal patients. The altered structure potentially changes their functioning on the ocular surface and can further the development of dry eye (Danjo et al., 1998, Invest Ophthalmol Vis Sci 39: 2602–2609).

Role of Galectins in Tear Film Insufficiency

Galectins are carbohydrate-binding proteins that may have the potential to serve as ideal candidates to promote the spreading of the tear film onto the corneal and conjunctival surface. These proteins bind with high affinity to the mucins, specifically to their O-linked carbohydrate side chains. Without being bound by any particular theory or mechanism of action, galectins can promote tear film spreading by binding secretory mucins to transmembrane mucins (or other glycoproteins) on the surface of the cornea and conjunctiva. In mucin-deficient eyes, exogenous galectins may prolong or enhance mucin binding. Furthermore, galectins may in themselves serve to promote more even spreading of the tear film by binding to corneal surface carbohydrate-binding proteins, even in a mucin-deficient environment.

The interaction between mucins and galectins has been demonstrated in non-ocular tissues. Galectins have shown to modulate mucin expression and production with strong binding affinity to various mucins. Galectin-3 binds to and modulates the expression of mucin derived from human colon cancer cells in a concentration-dependent manner (Bresalier et al., 1996, Cancer Res 56: 4354–4357; Dudas et al., 2002, Gastroenterology 118: 1553). In ovarian tumor cells, the mucin-like glycoprotein CA125 binds to galectin-1 (Seelenmeyer et al., 2002, J Cell Sci, 116:1305–1318).

Galectins constitute a family of widely distributed carbohydrate binding proteins characterized by their affinity for β-galactoside-containing glycans found on many cell surface and ECM glycoproteins. In mammals, there are currently 14 members of the galectin family (galectin-1 to -14) defined by structural similarities in their carbohydrate-recognition domains (CRD). Galectins are soluble proteins. Intracellularly, they reside largely in the cytoplasm, and galectins-1 and -3 have been detected in the nuclei of proliferating cells. Extracellularly, they have been found on cell surface and in the ECM. Like certain growth factors (e.g. bFGF) and cytokines (e.g. IL-1), galectins do not contain a classical signal sequence or a transmembrane domain and are secreted from the cell via a nonclassical pathway which is not well understood. Some galectins such as galectins-1, -3, -8 and -9 have wide tissue distribution, whereas others such as galectins-4, -5 and -6 exhibit tissue specificity. Galectins-1 and -3 are the two most extensively studied galectins. Extracellularly, both lectins are thought to play roles in cell-cell and cell-matrix adhesion by binding to oligosaccharides on distinct isoforms of fibronectin, laminin, vitronectin and integrins. Most galectins either have two CRDs or exist as homodimers and are functionally bivalent. The bivalent property may permit the lectin to interact with oligosaccharide chains of secretory mucin glycoproteins on one hand and the oligosaccharides of transmembrane mucins or other glycoprotiens on the apical surface of the cornea on the other, to promote the tearfilm spread on the ocular surface. Several studies have shown that galectin-3 is expressed in mouse and human corneal epithelium. Exogenous galectins-3 and -7 stimulate re-epithelialization of corneal wounds in a mouse animal model, and may play a role in corneal epithelial cell migration (Cao et al., 2002, J Biol. Chem. 277:42299–4230; 2003, Arch Ophthalmol, 121: 82–86).

In preliminary studies for the Examples herein using two different models of corneal wound healing, re-epithelialization of wounds was previously found to be significantly slower in galectin-3-deficient (gal3−/−) mice compared with wild-type (gal3+/+) mice. In contrast, there was no difference in corneal epithelial wound closure rates between galectin-1-deficient and wild-type mice. Exogenous galectin-3 and galectin-7 accelerated re-epithelialization of corneal alkali-burn wounds in a concentration-dependent manner. This effect was inhibited by the competing sugar, β-lactose, but not by an irrelevant disaccharide, sucrose (Cao et al., 2002, J Biol Chem. 277:42299–4230; 2003, Arch Ophthalmol, 121:82–86).

EXAMPLES

Materials and Methods

The following materials methods are used throughout the examples herein.

Artificial Tear Solutions with Therapeutic Concentrations of Galectins-1, -3, -7 and -8

A typical artificial tear solution is here formulated with galectin concentrations for animal studies. The solution are buffered, pH neutral, and isotonic, and include a thickening agent such as CMC or HMPC to increase the viscosity. Identical control solutions having all ingredients except galectins will also be made. The solutions are non-preserved, since preservatives can exacerbate epithelial damage. Therefore, fresh solutions will be made for each example, and are refrigerated between dosing. Different formulations include: Artificial tear control solution; Artificial tear solution containing 10 μg/mL of each of galectins -1, -3, -7, or -8, or pairwise combinations; and Artificial tear solution containing 20 μg/mL each of galectins -1, -3, -7, or -8, or pairwise combinations; and each of the above also containing 0.1 M β-lactose, a competitive disaccharide, which acts as a galectin inhibitor.

Scopolamine-Induced Tear Insufficiency in Normal Mice as an Animal Model of DES

Scopolamine is an anti-cholinergic agent targeting muscarinic cholinergic receptors. Transdermal scopolamine (scop) patches are commonly used for anti-nausea purposes and in treating motion sickness in humans. In a published study (Dursun et al., 2002, Invest Ophthamol & Vis Sci. 43:632–638), scop treatment in this manner resulted in a marked and statistically significant decrease in tear production to less than 20% of that found in the control group. Tear fluorescein clearance and corneal carboxyfluorescein uptake both increased approximately 3 fold. With further addition of placing the animals in a blower hood, these parameters increased even more dramatically. Additionally, conjunctival goblet cell density in the scop+ blower mice decreased more than 90% compared to the control group. Because the transdermal patch delivery system allows for controlled, sustained drug delivery, the decrease in tear production persists for over 24 hours, as opposed to topical atropine treatment, which has a duration of several hours. Reapplying a new scopolamine patch can further prolong the effect.

The C57BL/6 strain of mice (Charles River Laboratories, Wilmington, Mass.) are used in this example. The mice are 6 to 8 weeks old, and of mixed gender. Unanesthetized mice are restrained by hand to shave a 1-inch portion of the animals' midtail using an electric razor. Transdermal scop patches (Novartis, Summit, N.J.) are cut into 4 pieces, and a single quarter section is applied to the depilated midtail. Patches are reapplied after 48 hours to maintain a steady drug delivery. The animals are placed in a blower hood for 1 hour, 3 times per day for each day of the experiment.

MRL/lpr Autoimmune Mice

The MRL/Mp-lpr/lpr (MRL/lpr) strain of mice (Jackson Laboratory, Bar Harbor, Me.) is used in this experiment. These mice are congenic substrains, which develop autoimmune disease leading to lacrimal gland inflammatory lesions within 16 weeks of age. Based on the etiology and histologic evaluation, these mice have proposed as a model for human Sjögren's Syndrome (Jabs et al., 1991, Invest Ophthamol Vis Sci. 32:371–380; 2001, Curr Eye Res. 16:909–916). The mice in examples herein are at least 16 weeks old and of mixed gender.

Measurement of Tear Production, Tear Clearance, and Corneal Staining in Animals

Aqueous tear production is measured using phenol red impregnated cotton threads (Zone-quick, Oasis, Glendora, Calif.). The threads are held using forceps and will be applied to the ocular surface in the lateral canthus for 1 minute. Using the scale on the cotton threads, aqueous tear production is measured in millimeters of wetting of the thread.

Tear Break-up Time (TBUT) is determined using 2 μL of 1% sodium fluorescein (Alcon, Fort Worth, Tex.) applied in drop form to the ocular surface. The tear film is examined using a slit-lamp bio-microscope, and the length of time at which the film diffuses will be recorded.

Fluorescein staining is performed immediately after the TBUT measurement, by applying 2 μL of 1% sodium fluorescein in drop form to the ocular surface. Five minutes following application, corneal fluorescein staining will be evaluated using a slit-lamp bio-microscope. Fluorescein staining is commonly used in the clinic to assess corneal surface damage. It is expected that the corneal surface of animals with dry eye, but not normal corneal surfaces, will stain with fluorescein. The degree of fluorescein staining will be documented using a standardized F1 grading scale, similar to that used in clinical dry eye studies.

Equivalent Treatments

The treatment and measurement schedules are designed so that each of short-term (2 hours after galectin treatment) and long-term (~14 hours after galectin treatment) effects can be evaluated. It is anticipated that the galectins provide a long-term benefit following 4x/day treatment schedule. Modifications in treatment schedule, measurement schedule, or dose that are necessary to produce a beneficial effect on the cornea are within the equivalents of the examples herein. For example, if a response is seen with 20, but not 10 μL/mL galectin treatment, then an additional example comprises a higher dose (50 μg/mL).

Preparation of Galectin-1, -3, Galectin-7, and Galectin-8

It will be appreciated by one of ordinary skill in the art, that the galectins of this invention can be obtained from any available source. These include but are not limited to proteins isolated from natural sources, produced recombinantly or produced synthetically, e.g., by solid phase procedures. In accordance with the present invention, polynucleotide sequences which encode galectin-3, galectin-7 or galectin-8 may be used in recombinant DNA molecules that direct the expression of the galectins of this invention in appropriate host cells. Cherayil et al., supra, Madsen et al., supra, and Hadri et al., supra describe in detail the cloning of human galectin-1, -3, -7 and -8 respectively. In order to express a biologically active galectin-1, galectin-3, galectin-7 or galectin-8, the nucleotide sequence encoding galectin-1, galectin-3, galectin-7, galectin-8 or their functional equivalent, is inserted into an appropriate expression vector, i.e., a vector which contains the necessary elements for the transcription and translation of the inserted coding sequence. Methods which are well known to those skilled in the art can be used to construct expression vectors containing a galectin-1-encoding, galectin-3-encoding, galectin-7-encoding or galectin-8encoding sequence and appropriate transcriptional or translational controls. These methods include in vitro recombinant DNA techniques, synthetic techniques and in vivo recombination or genetic recombination. The introduction of deletions, additions, or substitutions can be achieved using any known technique in the art e.g., using PCR based mutagenesis. Such techniques are described in Sambrook et al., *Molecular Cloning: A Laboratory Manual*, Cold Spring Harbor Press, Plainview, N.Y., 1989 and Ausubel et al., *Current Protocols in Molecular Biology*, John Wiley & Sons, New York, N.Y., 1989. A variety of expression vector/host systems may be utilized to contain and express a galectin-1-encoding, galectin-3-encoding, galectin-7-encoding or galectin-8-encoding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti, pBR322, or pET25b plasmid); or animal cell systems. Alternatively, the galectins of the present invention could be produced using chemical methods to synthesize a galectin-1, galectin-3, galectin-7 or galectin-8 amino acid sequence, whole or in part. For example, peptide synthesis can be performed using various solid-phase techniques (Roberge et al., *Science* 269:202, 1995) and automated synthesis may be achieved, for example, using the 431 A peptide synthesizer (available from Applied Biosystems of Foster City, Calif.) in accordance with the instructions provided by the manufacturer.

Pharmaceutical Compositions

In one aspect of the present invention, pharmaceutical compositions are provided, wherein these compositions comprise galectin-1, galectin-3, galectin-7, and/or galectin-8, and optionally comprise a pharmaceutically acceptable carrier. In certain embodiments, these compositions optionally further comprise one or more additional therapeutic agents. In certain embodiments, the additional therapeutic agent or agents are selected from the group consisting of growth factors, anti-inflammatory agents, vasopressor agents, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), hepatocyte growth factor (HGF), B vitamins such as biotin, and hyaluronic acid.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences* Ed. by Gennaro, Mack Publishing, Easton, Pa., 1995 discloses various carriers used in formulating pharmaceutical compositions and known techniques for the preparation thereof. Some examples of materials which can serve as pharmaceutically acceptable carriers include, but are not limited to, sugars such as glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Therapeutically Effective Dose

In yet another aspect, according to the methods of treatment of the present invention, the treatment of dry eye by contacting the eye with a pharmaceutical composition, as described herein. Thus, the invention provides methods for the treatment of dry eye comprising administering a therapeutically effective amount of a pharmaceutical composition comprising active agents that include galectin-3, galectin-7 and/or galectin-8 to a subject in need thereof, in such amounts and for such time as is necessary to achieve the desired result. It will be appreciated that this encompasses administering an inventive pharmaceutical as a therapeutic measure to promote the spreading of tear film onto the corneal and conjunctival surface, or as a prophylactic measure to minimize complications associated with dry eye (e.g., as a wound irrigation solution during and/or following surgery or treatment of inflammatory conditions with antihistamines). In certain embodiments of the present invention a "therapeutically effective amount" of the pharmaceutical composition is that amount effective for promoting dry eye. The compositions, according to the method of the present invention, may be administered using any amount and any route of administration effective for treating the eye. Thus, the expression "amount effective for promoting the treating dry eye", as used herein, refers to a sufficient amount of composition to promote the tear film. The exact dosage is chosen by the individual physician in view of the patient to be treated. Dosage and administration are adjusted to provide sufficient levels of the active agent(s) or to maintain the desired effect. Additional factors which may be taken into account include the severity of the disease state, e.g., extent of dry eye, history of the condition; age, weight and gender of the patient; diet, time and frequency of administration; drug combinations; reaction sensitivities; and tolerance/response to therapy. Long acting pharmaceutical compositions might be administered several times a day, every day, 3 to 4 days, every week, or once every two weeks depending on half-life and clearance rate of the particular composition.

The active agents of the invention are preferably formulated in dosage unit form for ease of administration and uniformity of dosage. The expression "dosage unit form" as used herein refers to a physically discrete unit of active agent appropriate for the patient to be treated. It will be understood, however, that the total daily usage of the compositions of the present invention will be decided by the attending physician within the scope of sound medical judgment. For any active agent, the therapeutically effective dose can be estimated initially either in cell culture assays or in animal models, usually mice, rabbits, dogs, or pigs. The animal model is also used to achieve a desirable concentration range and route of administration. While direct application to the eye is envisioned as the route of administration, such information can then be used to determine useful doses and additional routes for administration in humans. A therapeutically effective dose refers to that amount of active agent that ameliorates the symptoms or condition. Therapeutic efficacy and toxicity of active agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosage for human use.

Administration of Pharmaceutical Compositions

After formulation with an appropriate pharmaceutically acceptable carrier in a desired dosage, the pharmaceutical compositions of this invention can be administered to humans and other mammals topically such as ocularly (as by powders, ointments, or drops), i.e., as applied directly to the eye. Alternative and additional routes such as orally, rectally, parenterally, intracisternally, intravaginally, intraperitoneally, bucally, or nasally, depending on the severity of the condition being treated, are envisioned.

Liquid dosage forms for ocular administration include buffers and solubilizing agents, preferred diluents such as water, preservatives such as thymosol, and one or more biopolymers or polymers for conditioning the solution, such as polyethylene glycol, hydroxypropylmethylcellulose, sodium hyaluronate, sodium polyacrylate or tamarind gum.

Liquid dosage forms for oral administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, ocular or cutaneous infections may be treated with aqueous drops, a mist, an emulsion, or a cream. Administration may be therapeutic or it may be prophylactic. Prophylactic formulations may be present or applied to the site of potential wounds, or to sources of wounds, such as contact lenses, contact lens cleaning and rinsing solutions, containers for contact lens storage or transport, devices for contact lens handling, eye drops, surgical irrigation solutions, ear drops, eye patches, and cosmetics for the eye area, including creams, lotions, mascara, eyeliner, and eyeshadow. The invention includes ophthalmological devices, surgical devices, audiological devices or products which contain disclosed compositions (e.g., gauze bandages or strips), and methods of making or using such devices or products. These devices may be coated with, impregnated with, bonded to or otherwise treated with a disclosed composition.

The ointments, pastes, creams, and gels may contain, in addition to an active agent of this invention, excipients such as animal and vegetable fats, oils, waxes, paraffins, starch, tragacanth, cellulose derivatives, polyethylene glycols, silicones, bentonites, silicic acid, talc, zinc oxide, or mixtures thereof.

Powders and sprays can contain, in addition to the agents of this invention, excipients such as talc, silicic acid, aluminum hydroxide, calcium silicates, polyamide powder, or mixtures of these substances. Sprays can additionally contain customary propellants such as chlorofluorohydrocarbons.

Transdermal patches have the added advantage of providing controlled delivery of the active ingredients to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of an active agent, it is often desirable to slow the absorption of the agent from subcutaneous or intramuscular injection. Delayed absorption of a parenterally administered active agent may be accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues.

Compositions for rectal or vaginal administration are preferably suppositories which can be prepared by mixing the active agent(s) of this invention with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

Uses of Pharmaceutical Compositions

As discussed above and described in greater detail in the Examples, galectin-3, galectin-7 and galectin-8 are useful as promoters of tear film spreading by binding to oligosaccharide chains of secretory mucins to the transmembrane muscins (or other glycoproteins). In general, it is believed that these galectins will be clinically useful in stimulating the healing of the dry eye.

In general, it is shown herein that these galectins are clinically useful in stimulating the healing associated with any epithelial tissue including but not limited to the skin epithelium; the corneal epithelium; the lining of the gastrointestinal tract; the lung epithelium; and the inner surface of kidney tubules, of blood vessels, of the uterus, of the vagina, of the urethra, or of the respiratory tract. The present invention encompasses in various embodiments the treatment of a variety of epithelial wound types including but not limited to surgical wounds, excisional wounds, blisters, ulcers, lesions, abrasions, erosions, lacerations, boils, cuts, sores, and burns resulting from heat exposure or chemicals. These wounds may be in normal individuals or those subject to conditions which induce abnormal wound healing such as diabetes, corneal dystrophies, uremia, malnutrition, vitamin deficiencies, obesity, infection, immunosuppression and complications associated with systemic treatment with steroids, radiation therapy, non-steroidal anti-inflammatory drugs (NSAID), anti-neoplastic drugs and anti-metabolites.

Galectins-1, -3, -7 and/or galectin-8 are, for example herein, useful to promote dermal re-establishment subsequent to dermal loss. Alternatively, galectin-1, galectin-3, galectin-7 and/or galectin-8 are shown herein to increase the adherence of skin grafts to a wound bed and to stimulate re-epithelialization from the wound bed. Suitable skin grafts include, but are not limited to, autografts, artificial skin, allografts, autodermic grafts, autoepidermic grafts, avacular grafts, Blair-Brown grafts, bone grafts, brephoplastic grafts, cutis grafts, delayed grafts, dermic grafts, epidermic grafts, fascia grafts, full thickness grafts, heterologous grafts, xenografts, homologous grafts, hyperplastic grafts, lamellar grafts, mesh grafts, mucosal grafts, Ollier-Thiersch grafts, omenpal grafts, patch grafts, pedicle grafts, penetrating grafts, split skin grafts, and thick split grafts.

Galectins-1, -3, -7 and/or galectin-8 are useful herein to treat dermatitis herpetiformis in which blisters form at the dermo-epidermal junction. Galectins-1, -3, -7 and/or galectin-8 are useful herein to treat epidermolysis bullosa, a defect in adherence of the epidermis to the underlying dermis which results in frequent, open and painful blisters, by accelerating re-epithelialization of these lesions. Galectins-1, -3, -7 and/or galectin-8 are further useful to treat pemphigus diseases that involve loss of cell-cell adhesion within the epidermis, or pemphigoid diseases that involve loss of cell-cell adhesion at the dermo-epidermal junction. Galectins-1, -3, -7 and/or galectin-8 are used to treat a variety of ulcers including but not limited to diabetic ulcers, dermal ulcers, decubitus ulcers, arterial ulcers, and venous stasis ulcers.

The present invention encompasses methods for the promotion of corneal tissue healing. This includes treating corneal epithelial defects caused by corneal ulcers, heat, radiation, phlyctenulosis, corneal abrasions or lacerations, photorefractive surgery for corrective myopia, foreign bodies and sterile corneal infiltrates; chemical burns caused by exposure to acids or alkali (e.g., hydrofluoric acid, formic acid, anhydrous ammonia, cement, and phenol) or other chemical agents such as white phosphorus, elemental metals, nitrates, hydrocarbons, and tar; keratopathies such as neurotrophic keratopathy, diabetic keratopathy and Thygeson's superificial punctate keratopathy; keratities such as viral keratitis (e.g., metaherpetic or herpetic keratitis) and bacterial keratitis; and corneal dystrophies such as lattice dystrophy, epithelial basement membrane dystrophy (EBMD) and Fuch's endothelial dystrophy.

Galectins-1, -3, -7 and/or galectin-8 are useful by methods herein to treat gastrointestinal ulcers and help heal the mucosal lining and regeneration of glandular mucosa and duodenal mucosal lining more rapidly. Inflammatory bowel diseases, such as Crohn's disease and ulcerative colitis, are diseases which result in destruction of the mucosal surface of the small or large intestine, respectively. Thus, galectins-1, -3, -7 and galectin-8 could be used to promote the resurfacing of the mucosal surface to aid more rapid healing and to prevent or attenuate progression of inflammatory bowel disease. Galectins-1, -3, -7 and galectin-8 are expected to bind mucin and facilitate its adhesion to the apical surface of the epithelium and could therefore be used to protect the gastrointestinal tract from injurious substances that are ingested or following surgery. Galectins-1, -3, -7 and/or galectin-8 could be used to reduce the side effects of gut toxicity that result from the treatment of bacterial infections, viral infections, radiation therapy, chemotherapy or other treatments. Galectins-8, -3 and/or galectin-7 can, for example, be used prophylactically or therapeutically to prevent or attenuate mucositis, esophagitis, or gastritis (e.g., to heal lesions associated with oral, esophageal, intestinal, colonic, rectal, and anal ulcers).

Galectins-1, -3, -7 and/or galectin-8 are useful to promote urothelial healing. Tissue layers comprising urothelial cells may be damaged by numerous mechanisms including catheterization, surgery, or bacterial infection (e.g., infection by an agent which causes a sexually transmitted disease, such as gonorrhea). The present invention also encompasses methods for the promotion of tissue healing in the female genital tract comprising the administration of an effective amount of galectins-8, -3 and/or galectin-7. Tissue damage in the female genital tract may be caused by a wide variety of conditions including infections with *Candida, Trichomonis, Gardnerella*, gonorrhea, *Chlamydia, Mycoplasma* infections and other sexually transmitted diseases.

Galectins-1, -3, -7 and/or galectin-8 are useful by methods herein to promote the repair of renal epithelial cells and, thus, could be useful for alleviating or treating renal diseases and pathologies such as acute and chronic renal failure and end stage renal disease. Galectins-1, -3, 7 and/or galectin-8 are useful by methods to promote the repair of breast tissue and therefore could be used to promote healing of breast tissue injury due to surgery, trauma, or cancer. Galectins-1, -3, -7 and/or galectin-8 are useful by methods herein to promote healing and alleviate damage of brain tissue due to injury from trauma, surgery or chemicals.

Galectins-1, -3, -7 and/or galectin-8 can be administered prophylactically to reduce or prevent damage to the lungs caused by various pathological states. For example, galectins -1, -3, -7 and/or galectin-8 can be used to promote the repair of alveoli and bronchiolar epithelium to prevent, attenuate, or treat acute or chronic lung damage. Emphysema, which results in the progressive loss of alveoli, and inhalation injuries, i.e., resulting from smoke inhalation and burns, that cause necrosis of the bronchiolar epithelium and alveoli can be effectively treated using galectins-1, -3, -7 and/or galectin-8 as can damage attributable to chemotherapy, radiation treatment, lung cancer, asthma, black lung and other lung damaging conditions.

It will be appreciated that the therapeutic methods encompassed by the present invention are not limited to treating wounds in humans, but may be used to treat wounds in any mammal including but not limited to bovine, canine, feline, caprine, ovine, porcine, murine, and equine species. When treating wounds in a given species, it is preferred, but not required, that the galectins-1, -3, -7 and/or galectin-8 used, have an amino acid sequence that is substantially identical to the amino acid sequence of galectins-1, -3, -7 and/or galectin-8 as it occurs naturally in the species.

All animal treatments described in these examples conformed to the Association for Research in Vision and Ophthalmology Resolution on the Use of Animals in Vision Research and the recommendations of the NIH Guide for the Care and Use of Laboratory Animals.

EXAMPLE 1

Up-regulation of Galectin-3 in Migrating Corneal Epithelium Following Injury

To determine whether the expression level of galectin-3 is altered in the epithelium of healing corneas following injury, mice corneas with 2 mm excimer laser ablations and abrasion wounds, were allowed to partially heal in vivo and were then processed for immunostaining with rat anti-human galectin-3 mAb M3/38 (American Type Culture Collection, Rockville, Md.). Corneal epithelium is a prototype-stratified squamous epithelium. In mouse, it constitutes 20–25% of total corneal thickness and is composed of 5 to 6 layers of cells. Posterior to the epithelial basement membrane is corneal stroma, which in mouse represents 70–80% of the total corneal thickness. Abrasion wounds remove epithelium leaving the corneal stroma intact. In contrast, excimer laser treatment, which is commonly used for correction of myopia, removes epithelium as well as anterior corneal stroma.

Swiss Webster mice (Taconic Laboratory Animal Services, Germantown, N.Y.) were anesthetized by an intramuscular injection of 1.25% avertin (0.2 ml/10 kg body weight). Avertin was prepared by mixing 2.5 g of 2,2,2 tribromoethanol, 5 ml 2-methyl-2-butanol (Aldrich, Milwaukee, Wis.) and 195 ml distilled water. Proparacaine eye drops (ALCAINE™ available from Alcon Labs, Fort Worth, Tex.) were applied to the cornea as topical anesthetic. Transepithelial excimer laser ablations were performed on the right eyes of a first group of mice (2 mm optical zone; 42 to 44 µm ablation depth, PTK mode) using an APEX PLUS™ excimer laser (Summit Technology of Waltham, Mass.). 2 mm abrasion wounds were produced on the right eyes of a second group of mice using an Alger brush (Alger Equipment Company of Lago Vista, Tex.).

Following surgery, all animals received an intramuscular injection of buprenorphine (0.2 ml of 0.3 mg/ml, BUPRENEX™ available from Reckitt & Colman Pharmaceuticals, Richmond, Va.) as a painkiller. Antibiotic ointment (VETROPOLYCN™ available from Pharmaderm, Melville, N.Y.) was applied and the corneas were allowed to partially heal in vivo for 16 to 18 hours. At the end of the healing period the animals were anesthetized as described above and were sacrificed by cervical dislocation. The eyes were then fixed in formalin for two hours prior to embedding in paraffin wax. Tissue sections (5 µm thick) were cut in the place parallel to the ocular axis. The sections were deparaffinized by treatment with xyline and re-hydrated with graded ethanol solutions (100%, 70%, and 30%). For immunostaining, tissue sections were incubated sequentially with 3% $H_2O_2$ (37° C., 10 min), and 2.5% normal goat serum to block endogenous peroxidase activity and nonspecific binding, respectively. The sections were subsequently incubated with mAb M3/38 (undiluted hybridoma fluid, 1 hour), biotinylated anti-rat IgG for 1 hour (1:200, Vector Labs, Burlingame, Calif.), a freshly prepared complex of avidin D and biotinperoxidase for 20 hours (Vector Labs) and diaminobenzidine (DAB)-$H_2O_2$ reagent (Kirkegaard & Perry Labs, Gaithersburg, Md.). For negative controls, sections were treated with an irrelevant mAb or media alone.

As shown in FIG. 9, immunohistochemical staining of paraffin sections of normal (FIG. 9 A and B) and healing (FIG. 9 C and D) corneas indicated that in both models of corneal wound healing, the leading edge of the migrating epithelium of healing corneas stained more intensely with mAb M3/38 compared to the normal epithelium, especially in the basal and middle cell layers. In both healing as well as normal corneal epithelium, immunostaining was more intense at the site of cell-matrix attachment. While stromal cells of normal corneas did not react with mAb M3/38, cells in the anterior stroma under the healing corneas robustly expressed galectin-3, especially in the region under the migrating epithelium.

The galectin-3 immunoreactivity in corneal epithelium was similar when corneas were allowed to heal in serum-free Eagle's minimum essential medium containing nonessential amino acids, L-glutamine, antibiotics and 0.4% bovine serum albumin (BSA) in organ culture for 16 to 18 hours. However, anterior stroma of corneas that were allowed to heal in vitro lacked cells expressing galectin-3, suggesting that the galectin-3 positive cells seen in the stroma of corneas that were allowed to heal in vivo are most likely leukocytes and not keratocytes.

To determine whether the carbohydrate recognition domain of galectin-3 plays a role in corneal epithelial sheet migration following injury, corneas with 2 mm excimer laser and abrasion wounds were allowed to heal in organ culture in the presence and absence of the disaccharides β-lactose and sucrose. While β-lactose contains galactose and binds galectins, sucrose lacks galactose and does not bind galectins. In these experiments, the rate of re-epithelialization of corneal wounds was significantly slower in the presence of β-lactose, while sucrose had no effect. As shown in FIG. 10, healing rates expressed as $mm^2/h$ among the different groups (mean±SEM of at least two experiments) were: media alone, 0.088±0.003 (N=29); media plus β-lactose, 0.063±0.003 (N=19); media plus sucrose 0.084±0.004 (N=10).

EXAMPLE 2

Corneal Epithelial Wound Closure in Wild Type and Galectin-3 Deficient Mice

To determine whether the re-epithelialization of corneal wounds is impaired in galectin-3 deficient mice, four different models of corneal wound healing were used. Galectin-3 deficient mice (gal-3$^{-/-}$) were generated by targeted interruption of the galectin-3 gene as described in Hsu et al., *Am. J. Pathol.* 156:1073, 2000. Specifically, the region coding for the CRD was interrupted with a neomycin resistant gene. This involved substituting a 0.5 kb intron 4-exon 5 segment with the antibiotic resistant gene (neo). That the galectin-3 gene has been inactivated was confirmed by Southern blot as well as Western blot analysis.

Figure 11:
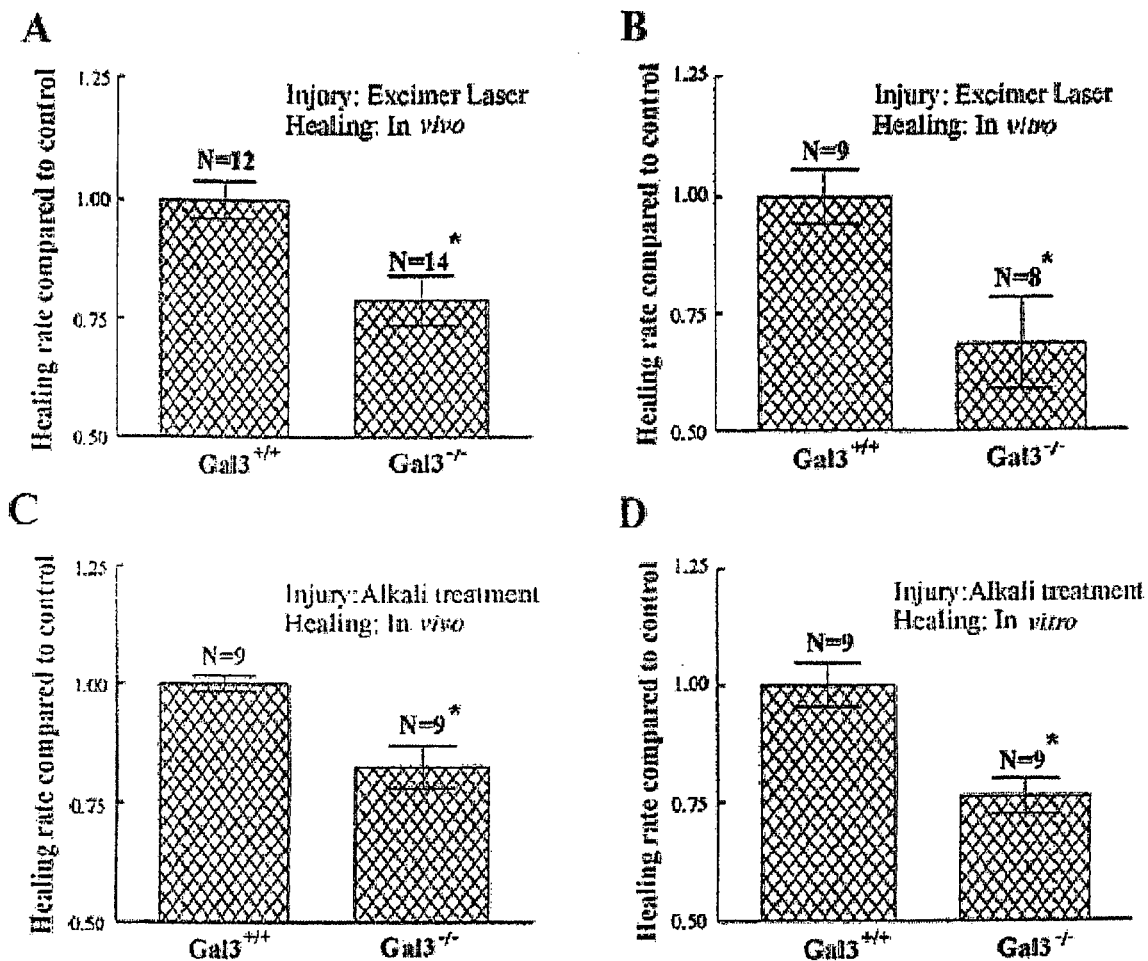
FIG. 11 is a series of graphs illustrating the healing rate of injured corneal epithelium in wild type (gal-3$^{+/+}$) and galectin-3 deficient (gal-3$^{-/-}$) mice injured by excimer laser or alkali treatment and allowed to heal in vivo or in vitro.

Briefly, corneas with excimer laser ablations (as described in Example 1) or alkali-burn wounds were allowed to partially heal in vivo or in vitro (as described in Example 1). For alkali injury, 2 mm filter discs (Whatman 50, Whatman International, Maidstone, UK) were prepared using a trephine, soaked in 0.5N NaOH, and placed on the surface of the cornea of the right eyes of a second group of mice for 30 seconds. The eyes were then rinsed with excess PBS. At the end of the healing period, the wound areas were visualized by staining with methylene blue. The stained wounds were then photographed at a standard distance, and the outlines of the wound areas were traced on paper from projected images of the stained wounds. These outlines were digitized and quantified using SIGMASCAN™ software (SPSS Science of Chicago, Ill.). Analysis of the wound closure rate in gal-3$^{+/+}$ mice in different models of wound healing revealed that wound closure rate expressed as mm$^2$/h in gal-3$^{+/+}$ mice was slower in corneas injured with an excimer laser compared to those injured with an alkali-burn. Also, regardless of the injury method used, the wound closure rate was faster in corneas allowed to heal in vivo compared to those in organ culture. As shown in FIG. 11, wound closure rates among gal-3$^{+/+}$ groups were: 0.076±0.003 mm$^2$/h for the excimer laser/in vivo group, 0.050±0.003 mm$^2$/h for the excimer laser/in vitro group, 0.182±0.003 mm$^2$/h for the alkali-burn/in vivo group, and 0.106±0.005 mm$^2$/h for the alkali-burn/in vitro group. Each group represents the mean±SEM of at least two experiments (N=9 or more in each group). Comparison of the wound closure rate of gal-3$^{+/+}$ groups with gal-3$^{-/-}$ groups revealed that regardless of whether the corneas were injured by excimer laser or by alkali treatment and whether the corneas were allowed to heal in vivo or in vitro, corneal epithelial wound closure rate expressed in mm$^2$/h was significantly slower in the gal-3$^{-/-}$ mice compared to that in the gal-3$^{+/+}$ mice. Wound closure rates among different gal-3$^{-/-}$ groups were 0.060±0.004 mm$^2$/h for the excimer laser/in vivo group, 0.036±0.005 mm$^2$/h for the excimer laser/in vitro group, 0.150±0.008 mm$^2$ for the alkali-burn/in vivo group, and 0.081±0.004 mm$^2$/h for the alkali-burn/in vitro group. Again, all values are the mean±SEM of at least two experiments (N=8 or more in each group).

EXAMPLE 3

Gene Expression Patterns in Migrating Corneal Epithelium of Galectin-3 Deficient Mice Following Injury In an attempt to understand why the re-epithelialization of corneal epithelial wounds is perturbed in gal-3$^{-/-}$ mice, gene expression patterns of healing gal-3$^{+/+}$ and gal-3$^{-/-}$ corneas were compared using cDNA microarrays and the results were further confirmed by semiquantitative RT-PCR.

Transepithelial excimer laser ablations (2 mm diameter) were produced on the right eye of 30 gal$^{+/+}$ and 30 gal$^{-/-}$ mice as described in Example 1. Corneas were allowed to partially heal in vivo for 20 to 24 hours. At the end of the healing period, animals were sacrificed and the corneas were excised and immediately placed in liquid nitrogen and shipped to Clontech Laboratories, Palo Alto, Calif. for analysis of gene expression using SMART™ cDNA technology. Briefly, total RNA was isolated using the reagents provided in the ATLAS™ Pure Total RNA Labeling System. Yield of RNA from the 30 gal-3$^{+/+}$ and 30 gal-3$^{-/-}$ corneas was 3.5 μg and 2.6 μg respectively. The A260:A280 ratio of the RNA preparations of the corneas of gal-3$^{+/+}$ and gal-3$^{-/-}$ mice were 1.48 and 1.37 respectively. The ribosomal RNA 28S: 18S ratio was 1.8 for both preparations. This ensured that the quality of RNA preparation was satisfactory. For probe preparation, first strand cDNA was synthesized using 175 ng of RNA, a modified oligo(dT) primer (the CDS primer), POWERSCRIPT™ reverse transcriptase, and SMART™ II oligonucleotides. Controls involved incubation of samples without reverse transcriptase. The cDNA was amplified by long distance (LD)-PCR. To determine the optimal number of amplification cycles, aliquots of reaction products were collected at 15, 18, 21 and 24 cycles and were analyzed by agarose gel electrophoresis. The yield of amplified double stranded cDNA using an optimal number of cycles, i.e., 23, was between 1 and 1.6 μg. The amplified cDNAs (500 ng) were radiolabeled using Klenow enzyme and $^{33}$P-αATP as described in the instruction manual for SMART™ cDNA probe synthesis for ATLAST microarrays (Clontech). The labeled probes were purified by filtration on a NUCLEOSPIN™ filter and were then hybridized to mouse 1.2k-I ATLAS™ nylon cDNA microarrays (Clontech). This is a broad spectrum array consisting of ~1200 mouse genes. Following hybridization, the membranes were exposed to a phosphorimager screen and the results were analyzed by ATLAS IMAGE™ 2.0 software (Clontech). The data were verified by semiquantitative RT-PCR.

Figure 12:
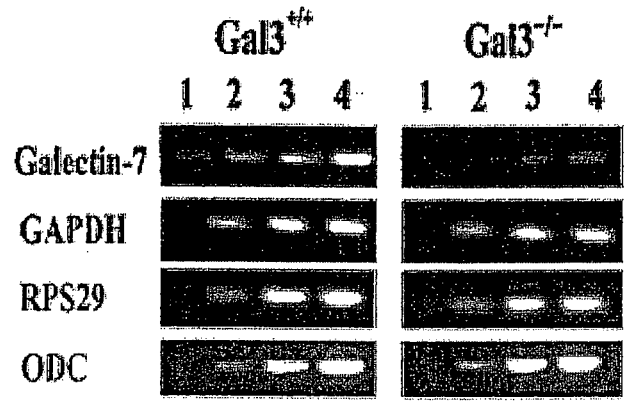
FIG. 12 is a table depicting differences in gene expression of galectin-7 and a selection of house keeping genes (GAPDH is D-glyceraldehyde-3-phosphate dehydrogenase; RPS29 is ribosomal protein S29; ODC is ornithine decarboxylase) between wild type (gal-3$^{+/+}$) and galectin-3 deficient (gal-3$^{-/-}$) mice as determined by cDNA microarray and semi-quantitative PCR.

For RT-PCR, total RNA and first strand cDNA were prepared from healing gal-3$^{+/+}$ and gal-3$^{-/-}$ corneas using the procedures described earlier. PCR amplification was performed in 50 μl volume using 14 ng of cDNA, gene-specific custom primers purchased from Clontech and other reagents from the ADVANTAGE™ 2 PCR kit (Clontech). The annealing temperature used was 68° C. and reactions were subjected to varying number of cycles of PCR amplification. For analysis of housekeeping genes, 5 μl aliquots of amplified product were collected at every 5$^{th}$ cycle, beginning at the 18$^{th}$ cycle, whereas for analysis of differentially expressed genes reaction amplified products were collected at every other cycle, beginning at the 28$^{th}$ cycle. Amplified products collected at various cycles were analyzed by electrophoresis in 1.5% agarose/ethedium bromide gels (FIG. 12).

These experiments revealed that compared to healing corneas of gal-3$^{+/+}$ mice, healing corneas of gal-3$^{-/-}$ mice contain markedly reduced levels of mRNA transcripts for galectin-7, another galactose-binding protein, and tolloid-like protein (TLL), a metalloproteinase. Overall, compared to healing gal-3$^{+/+}$ corneas, healing gal-3$^{-/-}$ corneas contained about 12 times less galectin-7 (FIG. 12) and 14 times less TLL gene transcripts (data not shown). Expression levels of mRNA transcripts of various housekeeping genes were similar in both healing gal-3$^{+/+}$ and gal-3$^{-/-}$ as detected by both microarray technology (FIG. 12), and semi-quantitative RT-PCR (FIG. 12, GAPDH is D-glyceraldehyde-3-phosphate dehydrogenase; RPS29 is ribosomal protein S29; ODC is ornithine decarboxylase).

Figure 13:
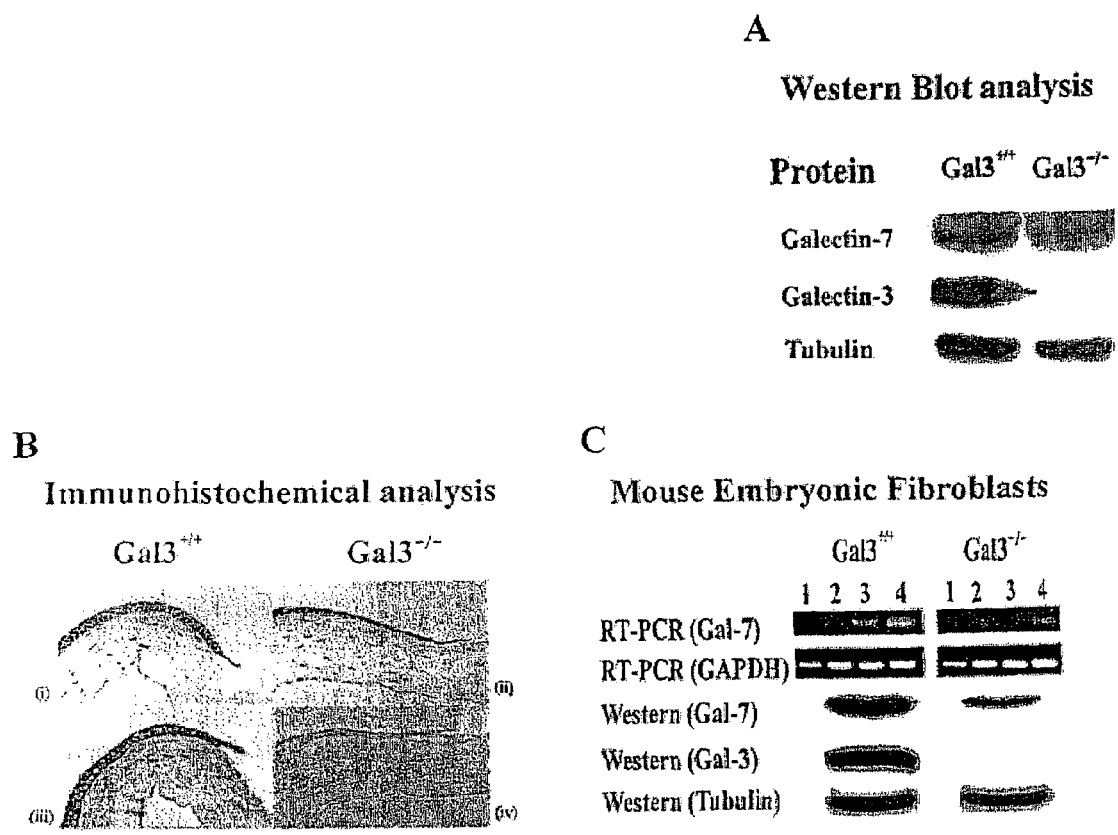
FIG. 13 illustrates differences in the expression of galectin-7 between wild type (gal-3$^{+/+}$) and galectin-3 deficient (gal-3$^{-/-}$) mice as determined by (A) western blot analysis, (B) immunohistochemical analysis, and (C) using mouse embryonic fibroblasts.

To determine whether the expression level of the galectin-7 protein is also reduced in healing corneas of gal-3$^{-/-}$ mice, western blot analysis using detergent extracts of healing gal-3$^{+/+}$ and gal-3$^{-/-}$ corneas (FIG. 13A) and immunohistochemical studies with an anti-galectin-7 polyclonal antibody using paraffin sections derived from corneas of gal-3$^{+/+}$ and gal-3$^{-/-}$ mice (FIG. 13B) were performed. The immunoreactivity was graded as intense (+++), moderate (++), weak (+) or negative (−). Significantly less galectin-7 immunoreactivity was detected in migrating epithelia of healing gal-3$^{−/−}$ corneas compared to those of healing gal-3$^{+/+}$ corneas: gal-3$^{+/+}$:+++36/42, ++5/42; + or less 1/42; gal-3$^{−/−}$:+++3/42, ++26/42, + or less 13/42. Also, gal-3$^{−/−}$ mouse embryonic fibroblasts (MEF) grown in cell culture expressed reduced levels of galectin-7 compared to gal-3$^{+/+}$ MEF cultures (FIG. 13C).

EXAMPLE 4

Exogenous Galectin-3 Stimulates the Re-epithelialization of Corneal Wounds in Wild Type and Galectin-3 Deficient Mice Having demonstrated that corneal epithelial wound closure rate is perturbed in gal-3$^{−/−}$ mice (Example 2), it was of interest to determine whether exogenous galectin-3 would stimulate the re-epithelialization of healing corneas in organ culture. In this study, corneas of gal-3$^{+/+}$ and gal-3$^{−/−}$ mice with alkali-burn wounds were incubated in serum free media in the presence and absence of varying amounts of recombinant galectin-3.

Recombinant full-length human galectin-3 was produced in *Escherichia coli* and purified as described previously (Yang et al., *Biochemistry* 37:4086, 1998). Alkali-burn wounds (2 mm diameter) were produced on both eyes of anesthetized mice using alkali-soaked filter discs as described in Example 2. Following injury, the animals were sacrificed and the eyes were excised and incubated in the presence or absence of exogenous galectin-3 for 18 to 20 hours. The left eyes of animals served as controls and were incubated in serum free media alone. The right eyes were incubated in serum free media containing various test reagents including: (i) galectin-3 (5 to 20 µg/ml), (ii) galectin-3 (10 µg/ml) plus 0.1 M β-lactose, (iii) galectin-3 (10 µg/ml) plus 0.1 M sucrose, (iv) 0.1 M β-lactose, or (v) 0.1 M sucrose. At the end of the healing period, the remaining wound areas were stained, photographed and quantified as described in Example 2 using SIGMASCAN™ software (SPSS Science of Chicago, Ill.). Each group contained a minimum of three eyes and all experiments were performed at least twice.

Figure 15:
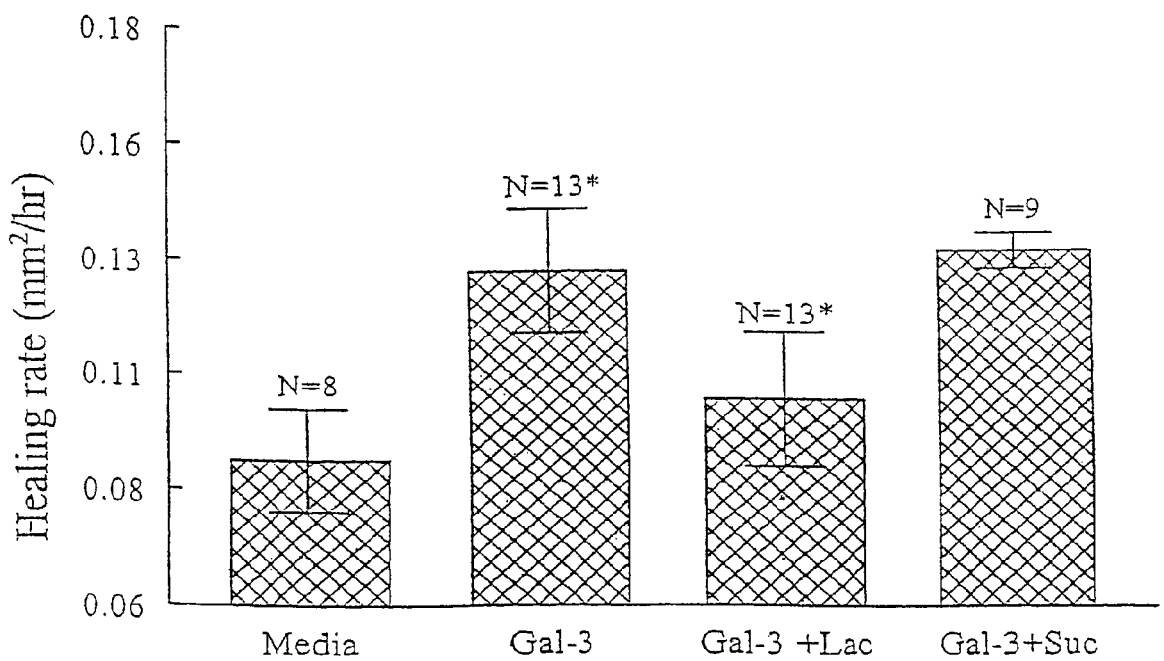
FIG. 15 is a graph illustrating the effect of β-lactose (Lac) and sucrose (Suc) on the healing rate of injured corneal epithelium of wild type (gal-3$^{+/+}$) mice in the presence of exogenous galectin-3.

The exogenous galectin-3 had no influence on the rate of re-epithelialization of corneal wounds in gal-3$^{−/−}$ mice (FIG. 14A), but it stimulated the rate of wound closure in a concentration-dependent manner in gal-3$^{+/+}$ mice (FIG. 14B) at 10 µg/ml and 20 µg/ml concentration (0 and 5 µg/ml: 0.090±0.010 mm$^2$/h; 10 µg/ml: 0.129±0.010 mm$^2$/h; 20 µg/ml: 0.154±0.004 mm$^2$/h; mean±SEM of at least two experiments, N=7 or more). As shown in FIG. 15, the stimulatory effect of galectin-3 on corneal epithelial wound closure in gal-3$^{+/+}$ mice was specifically inhibited by β-lactose but not sucrose (10 µg/ml galectin-3: 0.127±0.010 mm$^2$/h; 10 µg/ml galectin-3 plus 0.1 M β-lactose: 0.103±0.014 mm$^2$/h; 10 µg/ml galectin-3 plus 0.1 M sucrose: 0.130±0.003 mm$^2$/h. All values represent mean±SEM of at least two experiments, N=7 or more).

EXAMPLE 5

Exogenous Galectin-7 Stimulates the Re-epithelialization of Corneal Wounds in Wild Type and Galectin-3 Deficient Mice In a separate study, comparison of the gene expression patterns of normal and healing corneas of gal-3$^{+/+}$ mice using cDNA microarrays (i.e., as in Example 3) revealed that in healing corneas, expression of galectin-7 is markedly up-regulated. These findings in conjunction with the studies described in Example 3 showing that galectin-7 expression is down-regulated in the healing cornea of gal-3$^{−/−}$ mice, led to the design of experiments to determine whether exogenous galectin-7 would stimulate the re-epithelialization of healing corneas in organ culture. In this study, corneas of gal-3$^{−/−}$ mice with alkali-burn wounds were incubated in serum free media in the presence and absence of varying amounts of recombinant galectin-7.

Recombinant full-length human galectin-7 was produced in *Escherichia coli* by cloning the cDNA (available as an EST clone from American Type Culture Collection of Manassas, Va.) into the pET25b plasmid (available from Novagen, Madison, Wis.). Alkali-burn wounds (2 mm diameter) were produced on both eyes of anesthetized animals using alkali-soaked filter discs as described in Example 2. Following injury, the animals were sacrificed and the eyes were excised and incubated in the presence or absence of exogenous galectin-7 for 18 to 20 hours. The left eyes of animals served as controls and were incubated in serum free media alone. The right eyes were incubated in serum free media containing various test reagents including: (i) galectin-7 (20 µg/ml), (ii) galectin-7 (20 µg/ml) plus 0.1 M β-lactose, or (iii) galectin-7 (20 µg/ml) plus 0.1 M sucrose. At the end of the healing period, the remaining wound areas were stained, photographed and quantified as described in Example 2 using SIGMASCAN™ software (SPSS Science of Chicago, Ill.). Each group contained a minimum of six eyes and all experiments were performed at least twice.

As shown in FIG. 16, exogenous galectin-7 stimulated the rate of wound closure (media alone: 0.036±0.006 mm$^2$/h; 20 µg/ml galectin-7: 0.072±0.004 mm$^2$/h; mean±SEM of at least two experiments, N=10 or more). As shown in FIG. 16, the stimulatory effect of galectin-7 on corneal epithelial wound closure was specifically inhibited by β-lactose but not by sucrose (20 µg/ml galectin-7: 0.072±0.004 mm$^2$/h; 20 µg/ml galectin-7 plus 0.1 M β-lactose: 0.050±0.004 mm$^2$/h; 20 µg/ml galectin-7 plus 0.1 M sucrose: 0.079±0.007 mm$^2$/h. All values represent mean±SEM of at least two experiments, N=9 or more). As shown in FIG. 16, the rate of wound closure was further enhanced (0.094±0.003 gal-3$^{+/+}$ mm$^2$/h) when exogenous galectin-7 was added to the injured corneas of gal-3$^{+/+}$ mice instead of gal-3$^{−/−}$ mice.

EXAMPLE 6

Skin Epithelial Wound Closure in Wild Type and Galectin-3 Deficient Mice

Gal-3+/+ and gal-3$^{−/−}$ mice are anesthetized by an intraperitoneal injection of 1.25% Avertin (0.2 ml/10 g body weight). Prior to laser treatment, hair is shaved off from the dorsal region using a razor blade. Six millimeter transepithelial dorsal skin wounds are made using the excimer laser (Summit Technology of Waltham, Mass.). After surgery, antibiotic ointment is applied to the wound surface and buprenorphine (2 mg/kg body weight) is given subcutaneously to minimize post-surgical pain. The wounds are allowed to partially heal in vivo, and are examined 24, 48, and 72 hours after surgery. At the end of the healing period, the mice are again anesthetized by an intraperitoneal injection of 1.25% Avertin (0.2 ml/10 g body weight), wound areas are photographed and then quantitated using a Sigma scan software. The wound closure rates between the two groups of animals (i.e., gal-3$^{+/+}$ and gal-3$^{−/−}$ mice) are

EXAMPLE 7

Effect of Exogenous Galectin-3 on the the Re-epithelialization of Skin Wounds Animals (Mice: 57BL/6 and 129 mixed genetic background; Age: six to eight weeks old; Gender: mixed) are anesthetized by an intraperitoneal injection of 1.25% Avertin (0.2 ml/10 g body weight). Prior to laser treatment, hair is shaved off from the dorsal region using a razor blade. Two 6-mm transepithelial dorsal skin wounds (one on each side) are made using the excimer laser (Summit Technology of Waltham, Mass.). After surgery, antibiotic ointment is applied to the wound surfaces and buprenorphine (2 mg/kg body weight) is given subcutaneously to minimize post-surgical pain. The wounds are then allowed to partially heal in vivo. Every 4–6 hours, an ointment containing galectin-3 is applied to the right wound and carrier only is applied to the left wound which serves as a control. At the end of the healing period (24 to 48 hours), the animals are anesthetized by an intraperitoneal injection of 1.25% Avertin (0.2 ml/10 g body weight), wound areas are photographed and quantitated using a Sigma scan software. The wound closure rates between the two groups of animals (galectin-3 treated and control) are compared. The animals are then sacrificed by carbon dioxide inhalation or an overdose of pentobarbital.

EXAMPLE 8

Effect of Exogenous Galectin-7 on the the Re-epithelialization of Skin Wounds Animals (Mice: 57BL/6 and 129 mixed genetic background; Age: six to eight weeks old; Gender: mixed) are anesthetized by an intraperitoneal injection of 1.25% Avertin (0.2 ml/10 g body weight). Prior to laser treatment, hair is shaved off from the dorsal region using a razor blade. Two 6-mm transepithelial dorsal skin wounds (one on each side) are made using the excimer laser (Summit Technology of Waltham, Mass.). After surgery, antibiotic ointment is applied to the wound surfaces and buprenorphine (2 mg/kg body weight) is given subcutaneously to minimize post-surgical pain. The wounds are then allowed to partially heal in vivo. Every 4–6 hours, an ointment containing galectin-7 is applied to the right wound and carrier only is applied to the left wound which serves as a control. At the end of the healing period (24 to 48 hours), the animals are anesthetized by an intraperitoneal injection of 1.25% Avertin (0.2 ml/10 g body weight), wound areas are photographed and quantitated using a Sigma scan software. The wound closure rates between the two groups of animals (galectin-7 treated and control) are compared. The animals are then sacrificed by carbon dioxide inhalation or an overdose of pentobarbital.

EXAMPLE 9

Effect of Exogenous Galectin-8 or Galectin-1 on the Dry Eye in the Albino Rabbit Animals (Rabbits: albino; Age: six to eight weeks old; Gender: mixed) are anesthetized by an intraperitoneal injection of 1.25% Avertin (0.2 ml/10 g body weight). Each rabbit is induced to have dry eye by daily repeated instillations of 1.0% atropine sulfate (Burgalassi, S., et al., Ophthalm Res 31: 229–235, 1997). Evaluation of dry eye syndrome in each animal is assessed by the Schirmer I test and by examination of the cornea after fluorescein staining.

Every 4–6 hours, eyedrops containing a solution of galectin-8 are applied to the right eye of each animal, and carrier only is applied to the left eye which serves as a control. At the end of the healing period (24 to 48 hours), the animals are anesthetized by an intraperitoneal injection of 1.25% Avertin (0.2 ml/10 g body weight), eye areas are photographed and quantitated using a Sigma scan software. The surface of the eye and symptoms of dry eye are assessed between the two groups of eyes (galectin-8 treated right eyes and control left eyes) and these surfaces are compared. The animals are then sacrificed by carbon dioxide inhalation or an overdose of pentobarbital, and analyzed by standard toxicological criteria.

The amino acid sequences of various galectin-8 proteins (FIG. 18 and SEQ ID NOs: 4 and 5) of humans and other vertebrates (FIG. 20) are substantially identical, particularly those of other mammalian species. Similarly the amino acid sequences of various galectin-1 proteins (FIG. 19 and SEQ ID NO: 6) of humans and other mammals are substantially identical. The positions at which conservative and less conservation changes are observed indicate positions at which residues may be varied to obtain other functional galectin-8 and/or -1 proteins capable of remediating dry eye syndrome and other ocular indications.

EXAMPLE 10

Scopalomine Model: Galectin Treatment for DES and Effects of Pre-treatment with Galectin Solution Prior to Scopolomine Treatment Artificial tear solutions containing either 0, 10 or 20 µg of one or two of galectin-1, galectin-3, galectin-7 and galectin-8 per mL of solution will be administered according to the treatment schedule described below. One eye of each animal is treated at each time point, using a 10 µL drop volume. In a group of the scop patch model animals, 10 µg/mL galectin solution is applied to one eye 4 times daily, beginning immediately after application of the scop patch. Treatment groups of mice each are used. The treatment groups and eyes are randomized and coded such that the measurements are taken in a masked fashion. One eye of each animal receives a treatment solution, and the other receives control drops. Measurements are taken bilaterally at each time point.

EXAMPLE 11

Scopalomine Model: Combined Treatment of Galectins Administered with β-Lactose, a Galectin Inhibitor The same procedure as in Example 1 is performed, however with 10 µg/mL galectin solution combined with 0.1 M β-lactose, to determine whether the effects of the galectins can be inhibited by a competing disaccharide.

Treatment Schedule for Scopalamine Model

Day 1—Baseline measurements (tear production, TBUT, fluorescein staining) Scopolomine application Day 2—Pre-treatment measurements, 24 hours after scop application (Day 2, Time 0) Galectin or control treatment at 0, 4, 8 and 12 hours after measurements Blower hood exposure treatment between hours 1–2, 4–5, 8–9

Day 3—Apply new scop patch at time 0 Galectin or control treatment at time 0, 4, 8 and 12 hours Measurements (Day 3, Time 2 hrs) 2 hours after first treatment Blower hood exposure treatment between hours 1–2, 4–5, 8–9

Day 4—Measurements (Day 4, Time 0) Galectin or control treatment at time 0, 4, 8 and 12 hours Blower hood exposure treatment between hours 1–2, 4–5, 8–9

Day 5—Apply new scop patch at time 0 Galectin or control treatment at time 0, 4, 8 and 12 hours Blower hood exposure treatment between hours 1–2, 4–5, 8–9

Day 6—Measurements (Day 6, Time 0)

EXAMPLE 12

Role of Galectins-1, -3, -7 and -8 in DES: Autoimmune MRL/lpr Strain of Mice

Treatment groups and eyes are randomized and coded such that the measurements will be taken in a masked fashion. One eye of each animal receives either treatment or control drops. Measurements are taken bilaterally at each time point.

Treatment Schedule

Day 1—Baseline measurements (tear production, TBUT, fluorescein staining) Galectin or control treatment at time 0, 4, 8 and 12 hours Day 2—Galectin or control treatment at 0, 4, 8 and 12 hours Measurements (Day 2, Time 2 hrs) 2 hours after first treatment Day 3—Measurements (Day 3, Time 0) Galectin or control treatment at time 0, 4, 8 and 12 hours after measurements Day 4—Galectin or control treatment at time 0, 4, 8 and 12 hours Measurements (Day 4, Time 2 hrs) 2 hours after first treatment Day 5—Galectin or control treatment at time 0, 4, 8 and 12 hours Day 6—Measurements (Day 6, Time 0)

EXAMPLE 13

Remediation by Galectin-3 of Subjects Having a Dry Eye Syndrome

To determine the effect of a galectin on dry eye syndrome, an animal model system using interleukin-1 was employed, using four groups of mice with five animals in each group and treated as follows. In three of the groups, subjects were injected with interleukin-1 (IL-1) on Day 0, according to the standard procedure established for a murine model of Sjögren's syndrome (Zoukhri, D. et al., Invest Ophthalmol Vis Sci 42(5): 925–932). Control subjects received no injection and were not further treated with eye drops. The IL-1 recipients were then treated by administering tear drops containing galectin-3 at 75 µg/ml or at 150 µg/ml four times per day, commencing on Day 1. A group of subjects were similarly administered buffer only (without galectin) four times a day. The extent of the dry eye was evaluated by fluorescein clearance in each subject as described (Zoukhri et al.).

Figure 21:
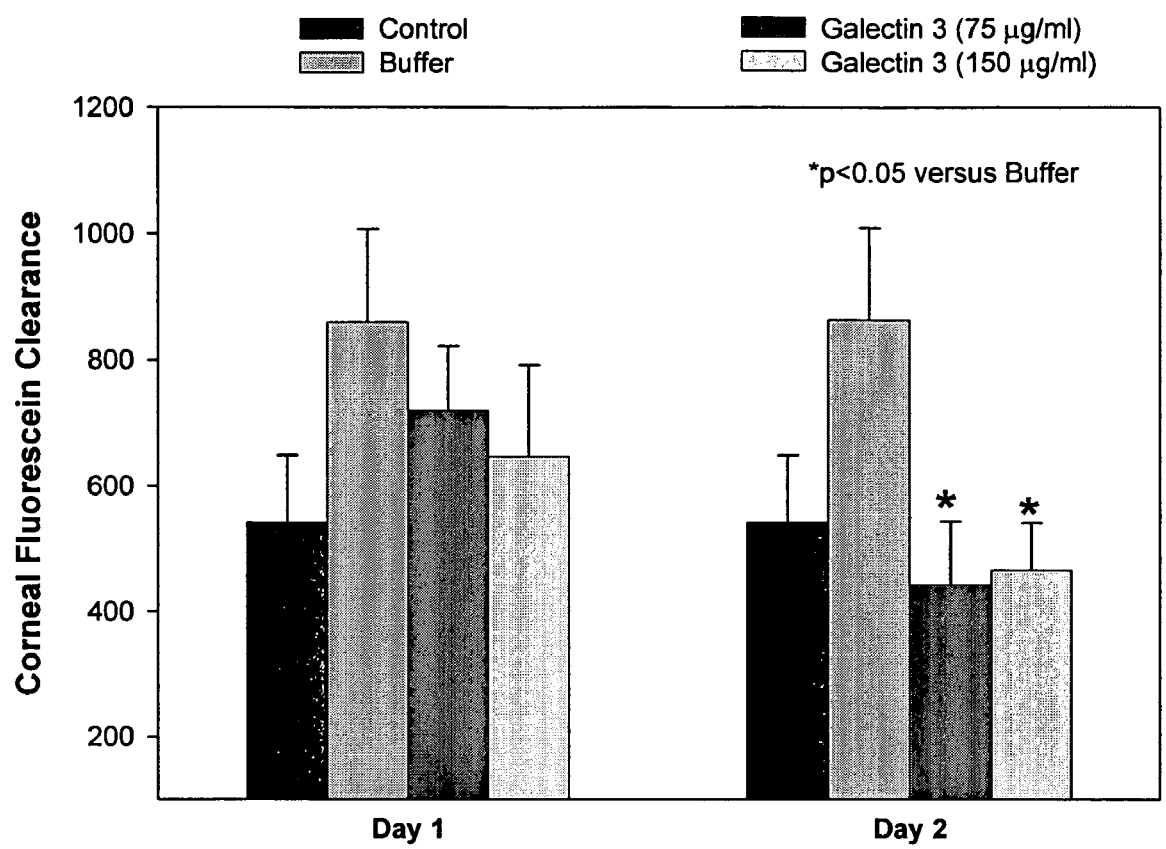
FIG. 21 is a bar graph showing effects of administration of a galectin on dry eye syndrome in a mouse model, the syndrome having been induced by injection of interleukin-1α (indicated as "IL-1" in the figure) on Day 0, as a function of time. Galectin-3 was administered on Days 1 and 2, four times a day, by tear drop to each of five subjects per group, the tear drops containing concentrations of 75 µg/ml or 150 µg/ml. Control group subjects were not injected with IL-1 and were not administered tear drops. Subjects in the "buffer" group were administered four treatments per day of the carrier vehicle only. Tear dynamics were evaluated by fluorscein clearance as in Zoukhri, D. et al., Invest Ophthalmol Vis Sci 42(5): 925–932, in which a lower value indicates a better tear flow. Data show that galectin treatment restored tear dynamics to that of the normal group, compared to control animals not administered the galectin, with data on treated compared to control having a statistical significance of $p<0.05$ on Day 2.

FIG. 21 shows that as early during treatment as Day 1, tear secretion as measured by fluorescein clearance was improved in subjects treated with galectin-3 at each of 75 µg/ml or at 150 µg/ml in comparison with control subjects, and the syndrome was entirely remediated in the galectin-treated subjects by day 2. In fact at day 2 somewhat better tear clearance was observed at the lower dose of 75 µg/ml, and an optimum dose may be even lower than this amount. The asterisks in FIG. 21 above the bars for the treated subjects at day 2 indicate that these data are statistically significant in comparison with data from the control group of subjects with dry eye and administered only the buffer vehicle, at a value of $p<0.05$. In conclusion, galectin-3 was capable of treating dry eye and remediating this condition within one to two days of treatment. Given the very high extent of galectin identity among mammals, and given the presence of galectin functional and specific amino acid sequence consensus identities between different members of the galectin family, it is anticipated that any of galectins-1, -3, -7 and -8, or combinations of these galectins, are similarly effective to remediate dry eye and related syndromes.

CONCLUSION

It is here demonstrated that galectin-3 and galectin-7 play a role in the re-epithelialization of corneal wounds. In Example 1 immunohistochemical studies revealed that following injury, galectin-3 is located in high density at sites of corneal epithelial cell-matrix adhesion, an ideal location for influencing cell-matrix interactions and hence cell migration. In Example 2, the re-epithelialization of corneal wounds was shown to be significantly slower in the galectin-3 deficient mice compared to that in wild-type mice. In Example 3, it was shown that following injury, expression levels of galectin-7 are significantly reduced in galectin-3 deficient mice compared to wild-type mice. In Examples 4 and 5, exogenous recombinant galectin-3 and galectin-7 were shown to stimulate the re-epithelialization of corneal wounds in gal3$^{+/+}$ mice. Examples 6–8 provide methods for measuring effects of galectins on re-epithelialization of wounds. Examples 9–12 provide methods for measuring effects of galectins on dry eye syndromes. Example 13 shows the rapid effective remediation of dry eye by galectin-3. It was further demonstrated in Example 1 that the stimulatory effect of galectin-3 on the rate of corneal epithelial wound closure was abrogated by a competing disaccharide (β-lactose) having the related galactoside chemical structure, but was not affected by an irrelevant chemically unrelated disaccharide (sucrose). This result shows that the carbohydrate recognition domain (CRD) is directly involved in the beneficial effect of the exogenous galectin on the cornea.

Without wishing to be bound to any particular theory regarding the mechanism by which galectins-1, -3, -7 and galectin-8 may influence remediation of dry eye syndromes, the following suggestions are presented.

As mentioned earlier, galectin-3 is thought to mediate cell-cell and cell-matrix interactions by binding to complementary glycoconjugates containing polylactosamine chains found in many ECM and cell surface molecules such as certain isoforms of fibronectin, laminin, and integrins (Liu, Clin. Immunol. 97:79, 2000 and Perillo, supra). However, the finding presented herein that exogenous galectin-3 does not accelerate the re-epithelialization of wounds in gal3$^{-/-}$ mice (see Example 4) suggests that intracellular galectin-3 contributes significantly to the process of wound healing, most probably, by influencing the expression of specific cell surface and/or ECM receptors, which in turn influence cell-matrix interactions and cell migration. This idea is consistent with published studies in which galectin-3 was stably overexpressed in breast carcinoma cell lines, resulting in elevated levels of α4β7 and α6β1 integrins and enhanced adhesion to various ECM molecules including laminin, fibronectin, and vitronectin as compared with parental cell lines expressing little or no galectin-3 (Warfield, supra and Mattarese, supra). In another study (Dudas et al., *Gastroenterology* 118:1553, 2000), colon cancer carcinoma cell lines transfected with galectin-3 expressed elevated levels of a specific mucin, MUC2, a major ligand of the lectin itself (Bresalier et al., *Cancer Research* 56:4354, 1996). The fact that the stimulatory effect of exogenous galectin-3 on the rate of re-epithelialization of wounds in gal3$^{+/+}$ mice is lactose inhibitable raises an intriguing possibility that intracellular galectin-3 may in fact regulate glycosylation of the proteins which serve as cell surface or ECM receptors of the lectin itself. That intracellular galectin-3 has the potential to act on the nuclear matrix to influence complex biological processes is also suggested by findings that under certain conditions the lectin can be found associated in the nucleus with ribonucleoprotein complexes and can act as a pre-mRNA splicing factor (Dagher et al., *Proc. Natl. Acad. Sci. USA* 92:1213, 1995). Also, Wang et al. have demonstrated that in prostate adenocarcinoma cells, galectin-3 is associated with the nuclear matrix and binds with both single-stranded DNA and RNA (Wang et al., *Biochem. Biophys. Res. Commun.* 217:292, 1995).

Analysis of gene expression patterns of corneas of healing gal3$^{+/+}$ and gal3$^{-/-}$ mice using mouse cDNA microarrays revealed that healing corneas of gal3$^{-/-}$ mice expressed markedly reduced levels of galectin-7 compared to those of wild-type mice (see Examples 3 and 5). Galectin-7 was first reported in 1994 (Barondes, supra) and is not as well characterized as galectin-3. Unlike galectin-3, galectin-7 exhibits a remarkable degree of tissue specificity. In adult animals, its expression is restricted to epithelia that are or are destined to become stratified (Timmons et al., supra). The protein is thought to be involved in cell-matrix and cell-cell interactions and in apoptosis (Leonidas, *Biochemistry* 37:13930, 1998 and Bernerd et al., *Proc. Natl. Acad. Sci. USA* 96:11329, 1999). In general, an inverse correlation exists between galectin-7 expression and keratinocyte proliferation, and galectin-7 expression is abrogated in SV40 transformed keratinocytes as well as in cell lines derived from epidermal tumors. The discovery described herein that exogenous galectin-3 does not stimulate re-epithelialization of wounds in gal3$^{-/-}$ corneas and that healing gal3$^{-/-}$ corneas contain reduced levels of galectin-7 suggests that galectin-3 may influence the re-epithelialization of wounds, at least in part, by modulating galectin-7. Indeed, it has been found that unlike galectin-3, galectin-7 accelerated re-epithelialization of wounds in gal3$^{-/-}$ corneas in a lactose-inhibitable manner. Also, mouse embryonic fibroblasts of gal3$^{-/-}$ mice expressed reduced level of galectin-7.

Regardless of the mechanisms involved, the findings that both galectin-3 and galectin-7 stimulate re-epithelialization of corneal wounds have broad implications for the treatment of epithelial wounds and non-healing epithelial wounds in particular. At present, treatment of persistent epithelial defects of the cornea is a major clinical problem. Moreover, the need continues for effective treatment of post-transplantation wounds, chronic wounds in the elderly, decubitus ulcers, and venous stasis ulcers of the skin. A number of growth factors (e.g., EGF, TGF, FGF, KGF, HGF) known to stimulate cell proliferation, have been tested for usefulness in corneal as well as cutaneous epithelial wound healing with overall disappointing results (Eaglstein, *Surg. Clin. North Am.* 77:689, 1997; Singer and Clark, *N. Engl. J. Med.* 341:738, 1999; Zieske and Gipson, pp. 364–372 in "Principle and Practice of Ophthalmology" Ed. by D. M. Albert and F. A. Jakobiec, W.B. Saunders Company, Philadelphia, Pa., 2000; Schultz et al., *Eye* 8:184, 1994; Kandarakiset al., *Am. J. Ophthalmol.* 98:411, 1984; and Singh and Foster, *Am. J. Ophthalmol.* 103:802, 1987). The extent of acceleration of re-epithelialization of wounds was far less in most of these studies using growth factors than that observed with galectins in the current study. Also, the epithelium of corneas treated with growth factors such as EGF is hyperplastic (Singh and Foster, *Cornea* 8:45, 1989), a clearly undesirable condition. In this respect, the clinical potential of galectin-3 and galectin-7 may be more attractive than that of growth factors because the lectins have not been shown to induce cell mitosis in epithelial cells. Over the last decade, the potential of excimer laser keratectomy to modify the corneal profile for correction of myopia has been realized. Thousands of such procedures are performed each week providing myopic individuals freedom from eyeglasses and contact lenses. In view of the fact that 25–30% of the adult population worldwide is myopic, it has been estimated that nearly half a million such procedures will be performed in the U.S. alone in a given year. In some cases, following excimer laser surgery, there is a delay in epithelial healing. Such a delay is highly undesirable because it puts the cornea at risk of developing postoperative haze, infectious keratitis and ulceration. Again, galectin-based treatments may help promote re-epithelialization of wounds in such cases.

OTHER EMBODIMENTS

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A method for treating or preventing dry eye syndrome in a mammal in need thereof, comprising administering to the mammal a therapeutically effective amount of a galectin protein.

2. The method according to claim 1, further comprising prior to administering, identifying the mammal in need of preventing dry eye syndrome.

3. The method according to claim 1, wherein the mammal in need of treating or preventing dry eye syndrome is characterized by at least one condition selected from the group consisting of: ocular epithelial wounds; prior usage of anti-histamine agents; prior usage of anti-inflammatory agents; and prior usage of excimer laser treatment.

4. The method according to claim 1, wherein the mammal is a human.

5. The method according to claim 1, wherein the galectin protein is selected from the group consisting of galectin-1, galectin-3, galectin-7, galectin-8 and combinations thereof.

6. The method according to claim 5, wherein the dry eye is a persistent syndrome.

7. The method according to claim 5, wherein the dry eye results in epithelial erosion.

8. The method according to claim 7, wherein the epithelial erosion produces a corneal wound.

9. The method according to claim 5, wherein the galectin-8 protein comprises the amino acid sequence of SEQ ID NO: 4 or 5.

10. The method according to claim 5, wherein the galectin-8 protein comprises an amino acid sequence that is substantially identical to the amino acid sequence of SEQ ID NO: 4 or 5.

11. The method according to claim 10, wherein substantially identical is having at least 60% identity, at least 70% identity, at least 80% identity, or at least 90% identity to the amino acid sequence of SEQ ID NO: 4 or 5.

12. The method according to claim 5, wherein the galectin-8 protein comprises a galectin-8 N-terminal domain and a galectin-8 proline, glycine, and tyrosine-rich domain and a galectin-8 galactoside-binding domain.

13. The method according to claim 5, wherein the galectin-3 protein comprises a galectin-3 proline, glycine, and tyrosine-rich domain and a galectin-3 galactoside-binding domain.

14. The method according to claim 5, wherein the galectin-7 protein comprises a galectin-7 N-terminal domain and a galectin-7 proline, glycine, and tyrosine-rich domain and a galectin-7 galactoside-binding domain.

15. The method according to claim 5, wherein the galectin-1 protein comprises a galectin-1 N-terminal domain and a galectin-1 proline, glycine, and tyrosine-rich domain and a galectin-1 galactoside-binding domain.

16. The method according to claim 5, wherein the galectin-7 protein comprises the amino acid sequence of SEQ ID NO: 2.

17. The method according to claim 5, wherein the galectin-7 protein comprises an amino acid sequence that is substantially identical to the amino acid sequence of SEQ ID NO: 2.

18. The method according to claim 17, wherein substantially identical is having at least 70% identity, at least 80% identity, or at least 90% identity to the amino acid sequence of SEQ ID NO: 2.

19. The method according to claim 5, wherein the galectin-3 protein comprises the amino acid sequence of SEQ ID NO: 1.

20. The method according to claim 5, wherein the galectin-3 protein comprises an amino acid sequence that is substantially identical to the amino acid sequence of SEQ ID NO: 1.

21. The method according to claim 20, wherein substantially identical is having at least 70% identity, at least 80% identity, or least 90% identity to the amino acid sequence of SEQ ID NO: 1.

22. The method according to claim 5, wherein the galectin-3 protein comprises a galectin-3 galactoside-binding domain.

23. The method according to claim 5, wherein the galectin-1 protein comprises the amino acid sequence of SEQ ID NO: 6.

24. The method according to claim 5, wherein the galectin-1 protein comprises an amino acid sequence that is substantially identical to the amino acid sequence of SEQ ID NO: 6.

25. The method according to claim 24, wherein substantially identical is having at least 60% identity, at least 70% identity, at least 80% identity, or least 90% identity to the amino acid sequence of SEQ ID NO: 6.

26. The method according to claim 5, wherein the galectin-1 protein comprises a galectin-1 galactoside-binding domain.

* * * * *

UNITED STATES PATENT AND TRADEMARK OFFICE
CERTIFICATE OF CORRECTION

PATENT NO.        : 7,189,697 B2                                                    Page 1 of 1
APPLICATION NO.   : 11/104677
DATED             : March 13, 2007
INVENTOR(S)       : Panjwani It is certified that error appears in the above-identified patent and that said Letters Patent is hereby corrected as shown below:

On column 1, lines 16-19, delete "This invention was made with Government support under grant number EY-07088 from the National Institutes of Health. Accordingly, the government may have certain rights in this invention."

and insert --This invention was made with Government support under grant numbers EY-09349 and EY-07088 from the National Institutes of Health. Accordingly, the government has certain rights in the invention.--

Signed and Sealed this

First Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,189,697 B2  
APPLICATION NO. : 11/104677  
DATED : March 13, 2007  
INVENTOR(S) : Panjwani Page 1 of 1

It is certified that error appears in the above-identified patent and that said Letters Patent is hereby corrected as shown below:

On column 1, lines 16-19, delete "This invention was made with Government support under grant numbers EY-09349 and EY-07088 from the National Institutes of Health. Accordingly, the government has certain rights in the invention."

and insert --This invention was made with government support under grant numbers EY-09349 and EY-07088 awarded by the National Institutes of Health. The government has certain rights in the invention.--

Signed and Sealed this  
Third Day of May, 2011

David J. Kappos  
*Director of the United States Patent and Trademark Office*